United States Patent
Choi et al.

(10) Patent No.: US 7,745,558 B2
(45) Date of Patent: Jun. 29, 2010

(54) ENTRAPPED β-CYCLODEXTRIN POLYMER AND A METHOD OF PREPARING THE SAME

(75) Inventors: Man Ho Choi, Seoul (KR); Dong Hyun Kim, Seoul (KR); Bong Chul Chung, Namyangju-si (KR); Ju-Yeon Moon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 293 days.

(21) Appl. No.: 11/947,035

(22) Filed: Nov. 29, 2007

(65) Prior Publication Data

US 2008/0194784 A1    Aug. 14, 2008

(30) Foreign Application Priority Data

Nov. 29, 2006   (KR) .................. 10-2006-0119300

(51) Int. Cl.
*C08F 251/00* (2006.01)
(52) U.S. Cl. .................................................. 527/300
(58) Field of Classification Search .................. 527/300
See application file for complete search history.

(56) References Cited

U.S. PATENT DOCUMENTS

| | | | | |
|---|---|---|---|---|
| 2,682,481 A | * | 6/1954 | Hewson | 427/336 |
| 3,420,788 A | * | 1/1969 | Solms | 524/48 |
| 3,472,835 A | * | 10/1969 | Buckler et al. | 536/46 |
| 4,432,802 A | * | 2/1984 | Harata et al. | 424/461 |
| 4,539,399 A | * | 9/1985 | Armstrong | 536/103 |
| 4,547,572 A | * | 10/1985 | Fenyvesi et al. | 536/103 |
| 4,673,707 A | * | 6/1987 | Tsai et al. | 525/54.2 |
| 4,902,788 A | * | 2/1990 | Zemel et al. | 536/123.1 |
| 5,008,195 A | * | 4/1991 | Allenza et al. | 435/193 |
| 5,075,432 A | * | 12/1991 | Vanzo | 536/103 |
| 5,357,012 A | * | 10/1994 | Nussstein et al. | 526/238.2 |
| 5,371,209 A | * | 12/1994 | Shieh et al. | 560/103 |
| 5,516,766 A | * | 5/1996 | Weisz et al. | 514/58 |
| 5,550,189 A | * | 8/1996 | Qin et al. | 525/54.3 |
| 5,681,828 A | * | 10/1997 | Pitha | 514/58 |

(Continued)

FOREIGN PATENT DOCUMENTS

JP       62275183 A    * 11/1987

(Continued)

OTHER PUBLICATIONS

Translation of JP 62275183 A (2009).*

(Continued)

*Primary Examiner*—Mark Eashoo
*Assistant Examiner*—Liam J Heincer
(74) *Attorney, Agent, or Firm*—Frommer Lawrence & Haug LLP; Ronald R. Santucci

(57) ABSTRACT

Provided are entrapped β-cyclodextrin polymers and a method of preparing the same. Particularly, entrapped β-cyclodextrin polymers are prepared by adding epichlorohydrin to β-cyclodextrin to prepare a polymer in a gel state, entrapping the polymer by entrapment of metal ions on the surface of the polymer and pulverizing the entrapped polymer to prepare powders. According to the entrapped β-cyclodextrin polymers, steroid hormones contained in a biological sample can be simply extracted without using an additional device required in conventional solid-phase extraction.

4 Claims, 20 Drawing Sheets

U.S. PATENT DOCUMENTS

| | | | |
|---|---|---|---|
| 5,730,969 A * | 3/1998 | Hora et al. | 424/85.1 |
| 5,935,941 A * | 8/1999 | Pitha | 514/58 |
| 6,001,821 A * | 12/1999 | Pitha | 514/58 |
| 6,048,736 A * | 4/2000 | Kosak | 436/536 |
| 6,420,129 B1 * | 7/2002 | Kimata et al. | 435/22 |
| 6,537,537 B2 * | 3/2003 | Deckner et al. | 424/78.02 |
| 6,583,248 B1 * | 6/2003 | Bowen | 526/238.2 |
| 6,660,804 B1 * | 12/2003 | Weltrowski et al. | 525/54.23 |
| 7,115,586 B2 * | 10/2006 | Loftsson | 514/58 |
| 2001/0008222 A1 * | 7/2001 | Ma et al. | 210/767 |
| 2002/0151523 A1 * | 10/2002 | Davis et al. | 514/58 |
| 2006/0134292 A1 * | 6/2006 | Abelyan et al. | 426/548 |
| 2007/0105192 A1 * | 5/2007 | Villafranca et al. | 435/69.1 |
| 2008/0194784 A1 * | 8/2008 | Choi et al. | 527/300 |
| 2008/0207931 A1 * | 8/2008 | Choi et al. | 552/545 |
| 2008/0275139 A1 * | 11/2008 | Gnaim | 514/773 |

FOREIGN PATENT DOCUMENTS

| | | |
|---|---|---|
| KR | 1997-037127 | 8/1997 |
| KR | 1997-037128 | 8/1997 |
| KR | 1997-0018599 | 5/1999 |

OTHER PUBLICATIONS

Cowie et al., Ion Conduction in Crosslinked Beta-cyclodextrin gels, Polymer vol. 39(26), 1998, 7139-7141.*

Liska, I. ;"Fifty years of solid-phase extraction in water analysis—historical development and overview", *Journal of Chromatography A*, 885 (2000) pp. 3-16.

Wells, Martha J.M. et al.; "Solid-phase extraction of acidic herbicides", *Journal of Chromatography A*, 885 (2000) pp. 237-250.

Ruiz-Gutierrez, V. et al. ; 'Update on solid-phase extraction for the analysis of lipid classes and related compounds' *Journal of Chromatography A*, 885 (2000) pp. 321-341.

Shimada, Kazutake et al.; "Gas chromatography and high-performance liquid chromatography of natural steroids" *Journal of Chromatography A*, 935 (2001) pp. 141-172.

Creaser, Colin S. et al.; "Immunoaffinity chromatography combined on-line with high-performance liquid chromatography-mass spectrometry for the determination of corticosteroids" *Journal of Chromatography A*, 794 (1998) pp. 37-43.

Choi, Man Ho et al.; "Determination of non-steroidal estrogens in breast milk, plasma, urine and hair by gas chromatography/mass spectrometry" *Rapid Communications in Mass Spectrometry*, 2002; 16; pp. 2221-2228.

Desroches, M.C. et al.; "Urinary 19-norandrosterone purification by immunoaffinity chromatography: application to gas chromatography/combustion/isotope ratio mass spectrometric analysis" *Rapid Communications in Mass Spectrometry*, 2002; 16; pp. 370-374.

Deventer, K. et al.; "Validation of a screening method for corticosteroids in doping analysis by liquid chromatography/tandem mass spectrometry" *Rapid Communications in Mass Spectrometry*, 2003; 17; pp. 2107-2114.

Kim, S.H. et al.; "Crosslinking of β-Cyclodextrin on Cholesterol Removal from Milk" *Archives of Pharm Res*, vol. 27, No. 11, 2004, pp. 1183-1187.

Kwak, H.S. et al.; Immobilized β-Cyclodextrin as a Simple and Recyclable Method of Cholesterol Removal in Milk *Archives of Pharm Res*, vol. 27, No. 8, 2004, pp. 873-877.

Forgo, Peter et al.; "Inclusion complexes of ketosteroids with β-cyclodextrin" *Steroids* 68 (2003) pp. 321-327.

Crini, Gregorio et al.; "Synthesis and applications of adsorbents containing cyclodextrins" *Journal of Separation Science* (2002), 25, pp. 789-813.

Zohrehvand, Shiva et al.; "2-Naphthol-containing β-cyclodextrin-epichlorohydrin copolymers: synthesis, characterization and fluorescence studies" *Polymer International* 54 (2005) pp. 744-753.

* cited by examiner

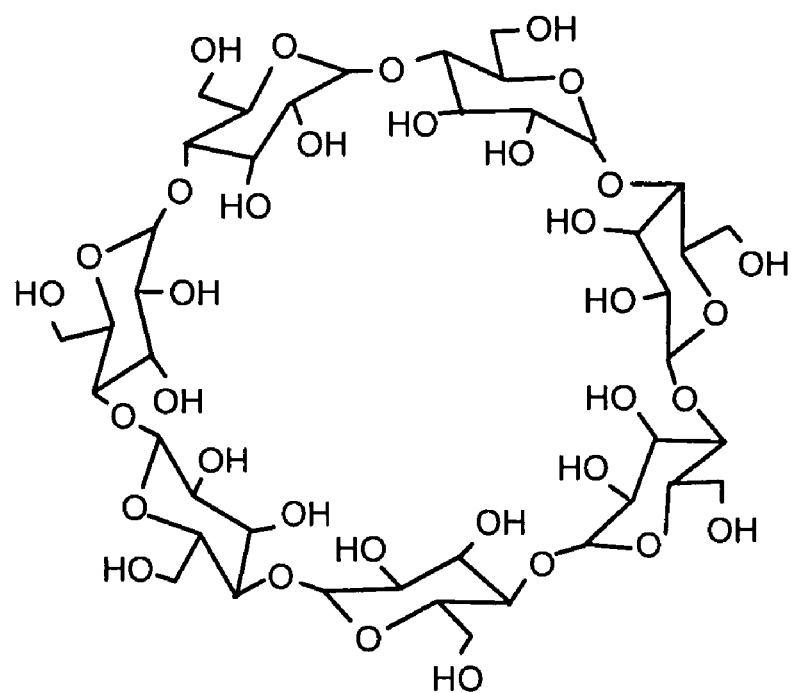
F I G. 1a
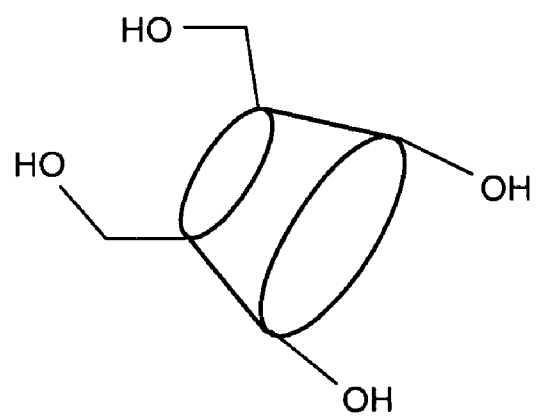
F I G. 1b

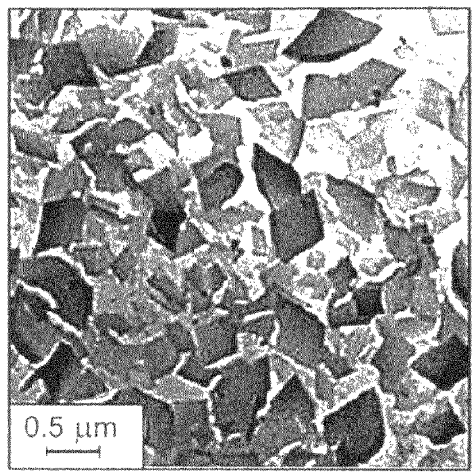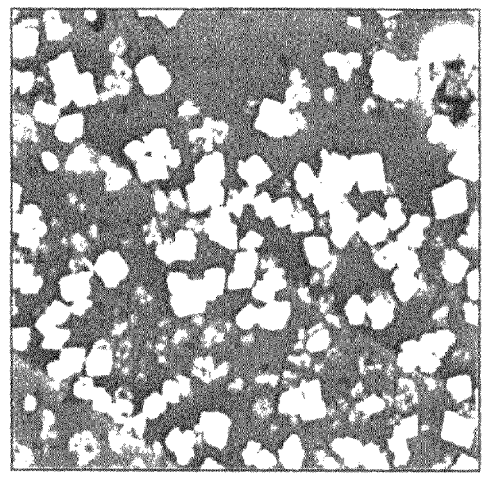
FIG. 3a    FIG. 3b
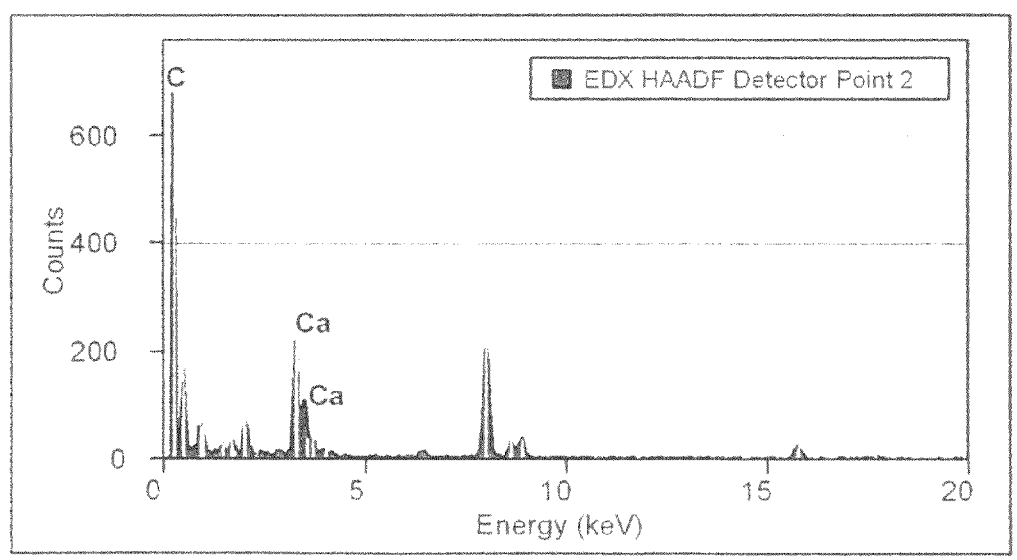
FIG. 3c

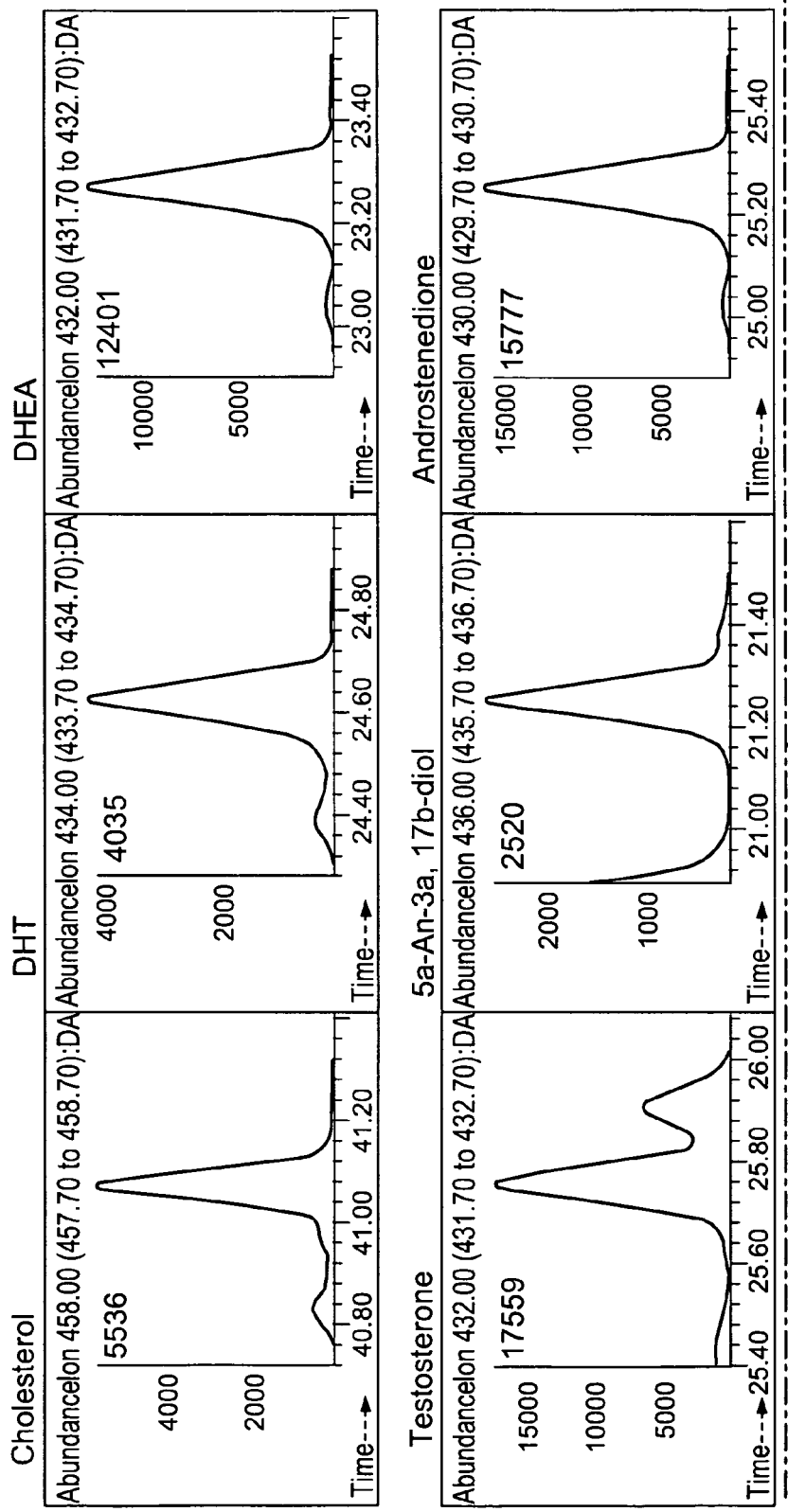
FIG. 4a1

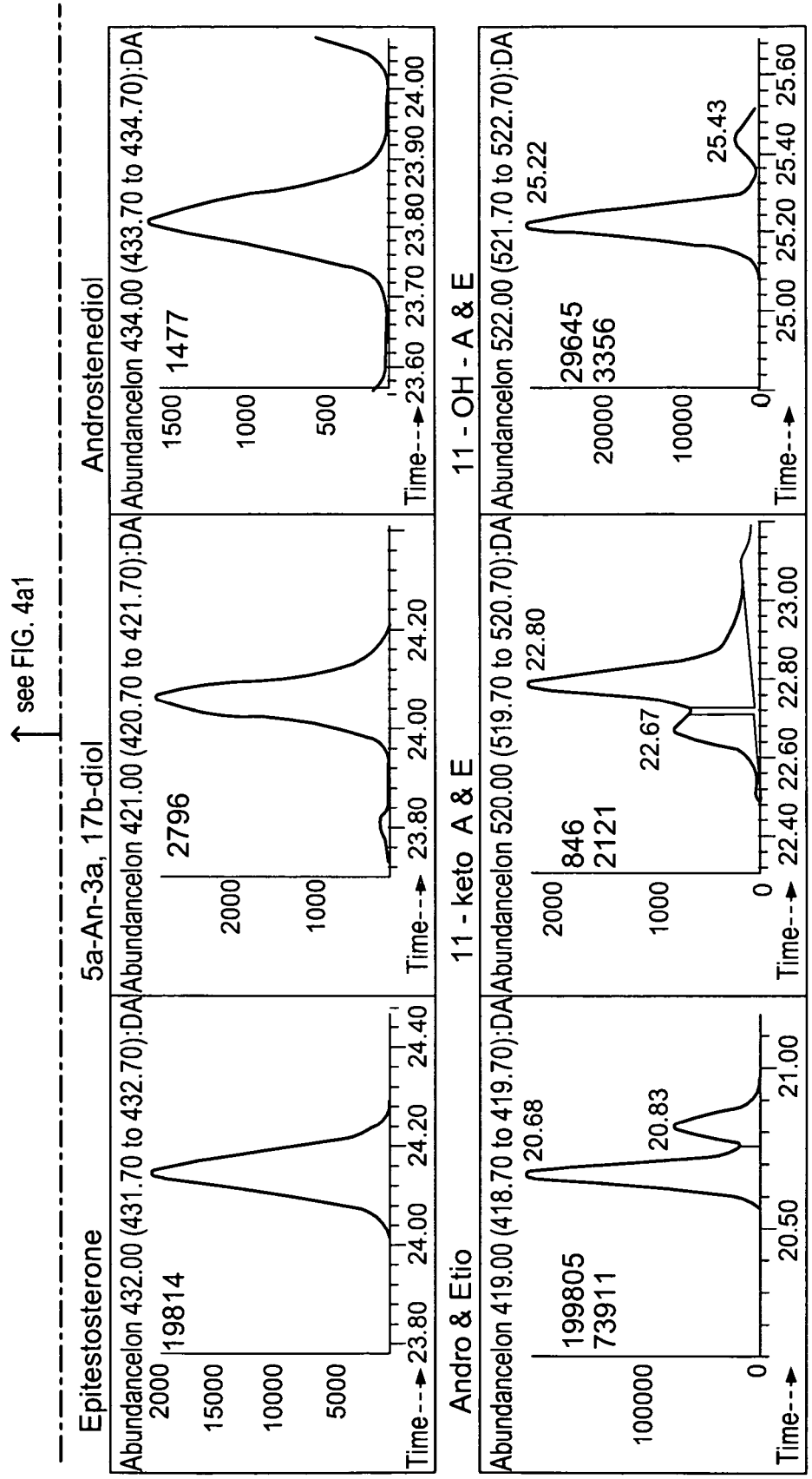
FIG. 4a2

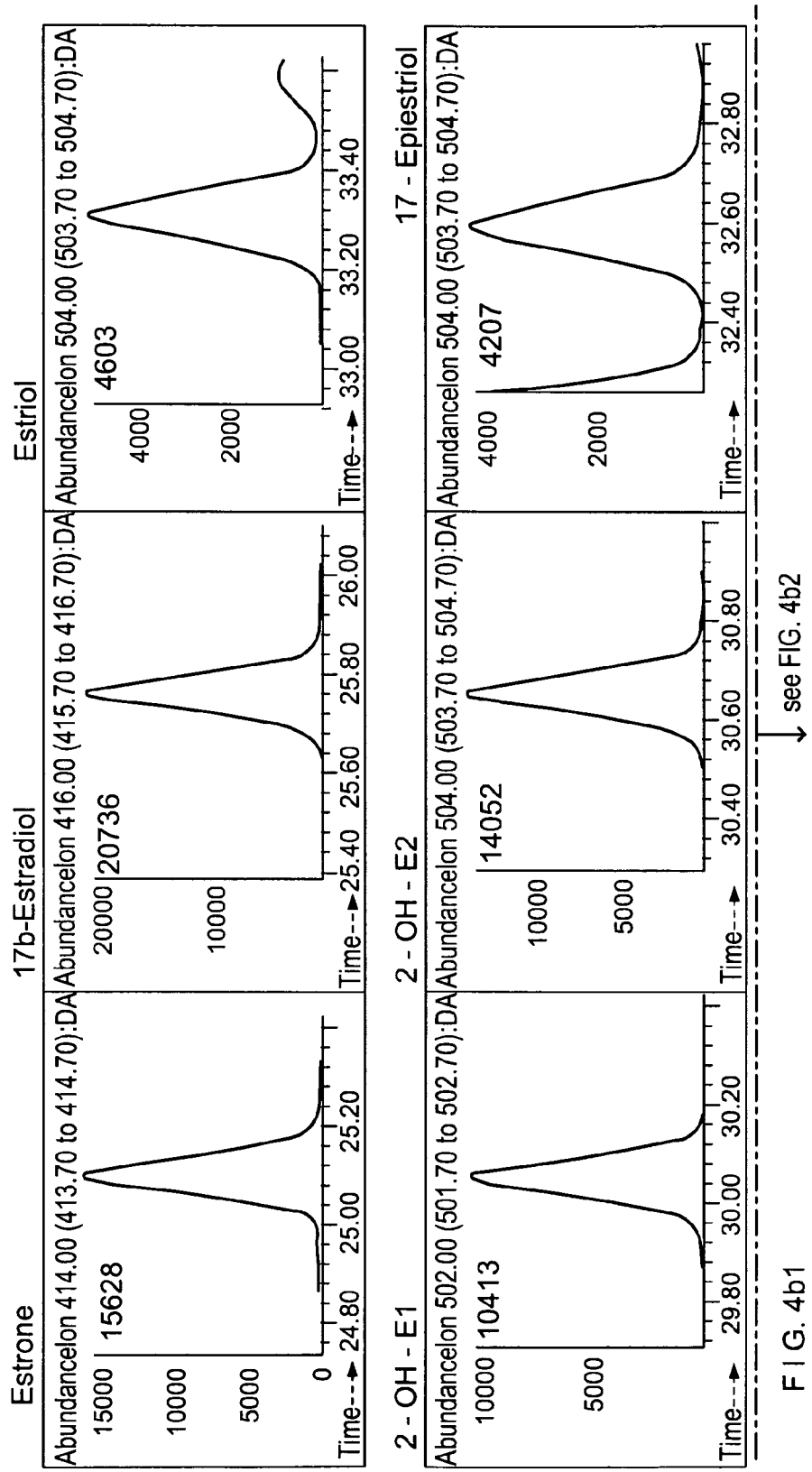
FIG. 4b1

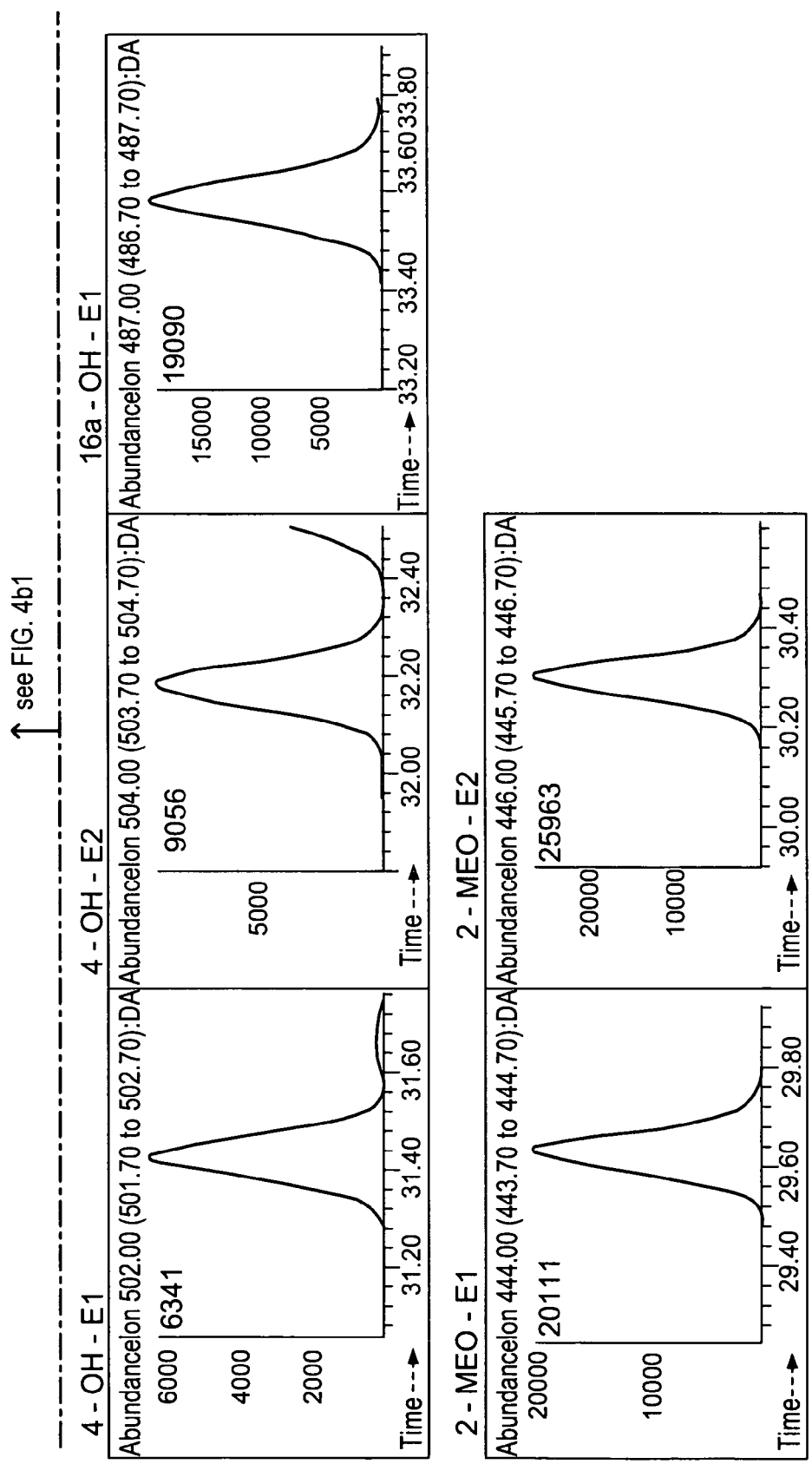
FIG. 4b2

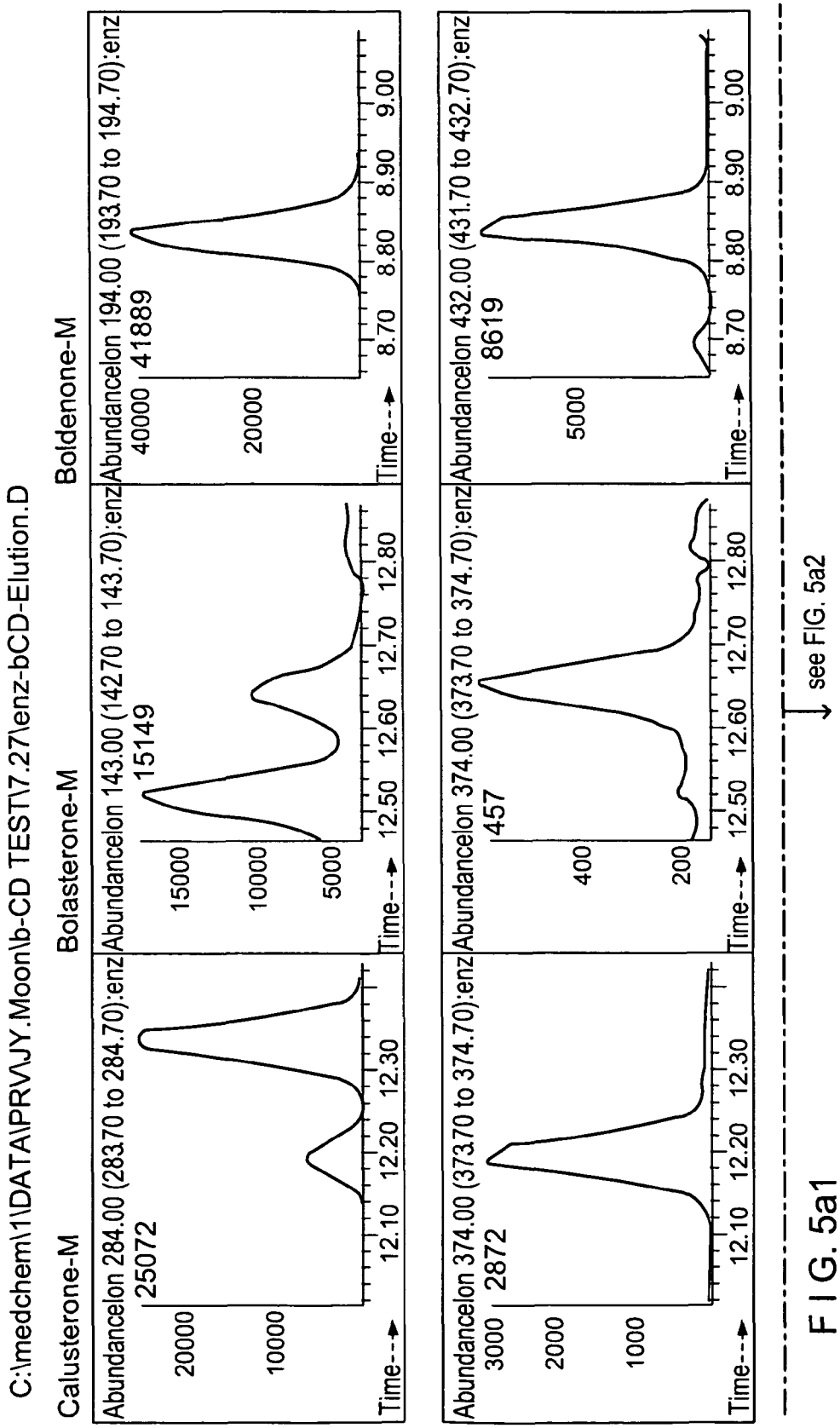
FIG. 5a1

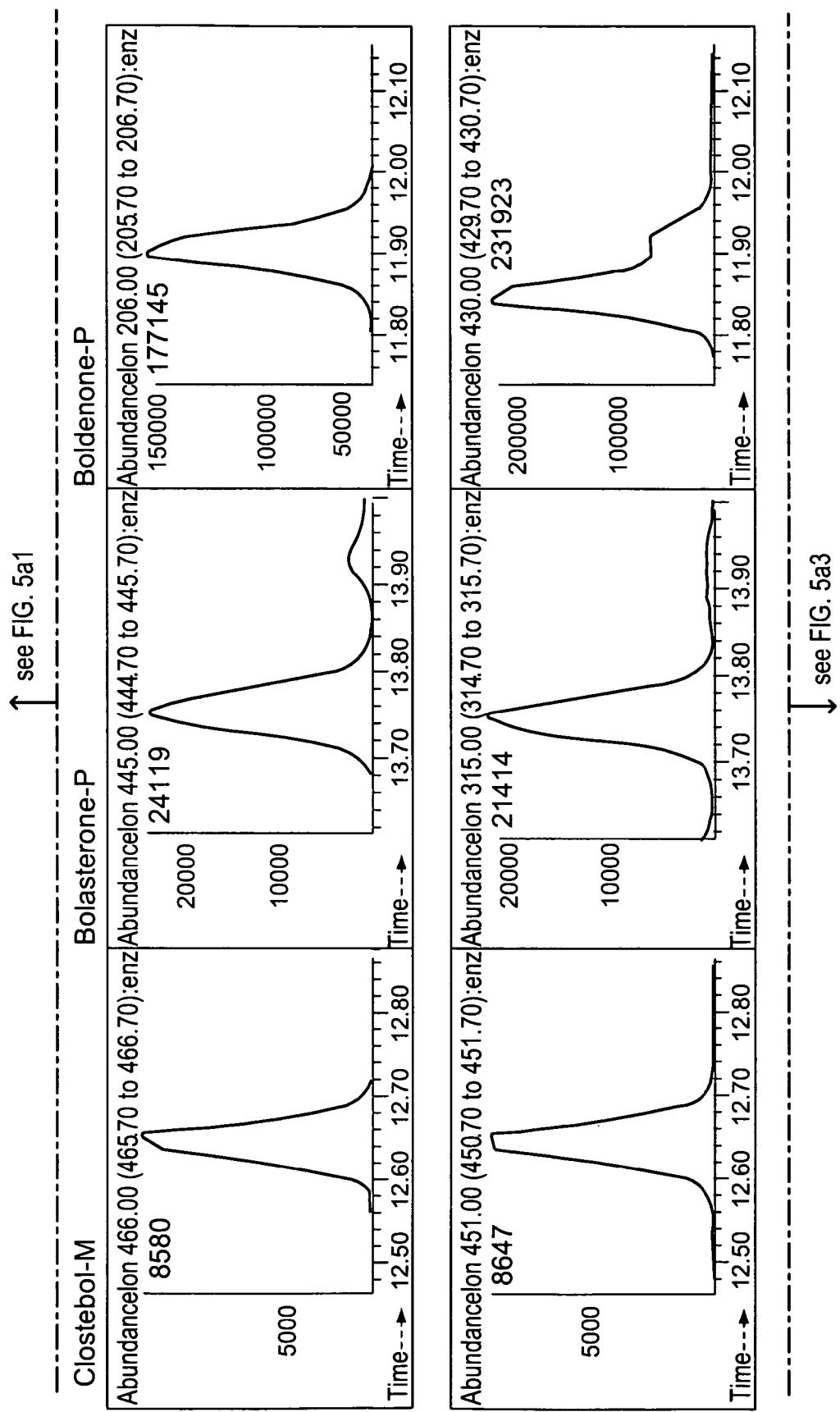
FIG. 5a2

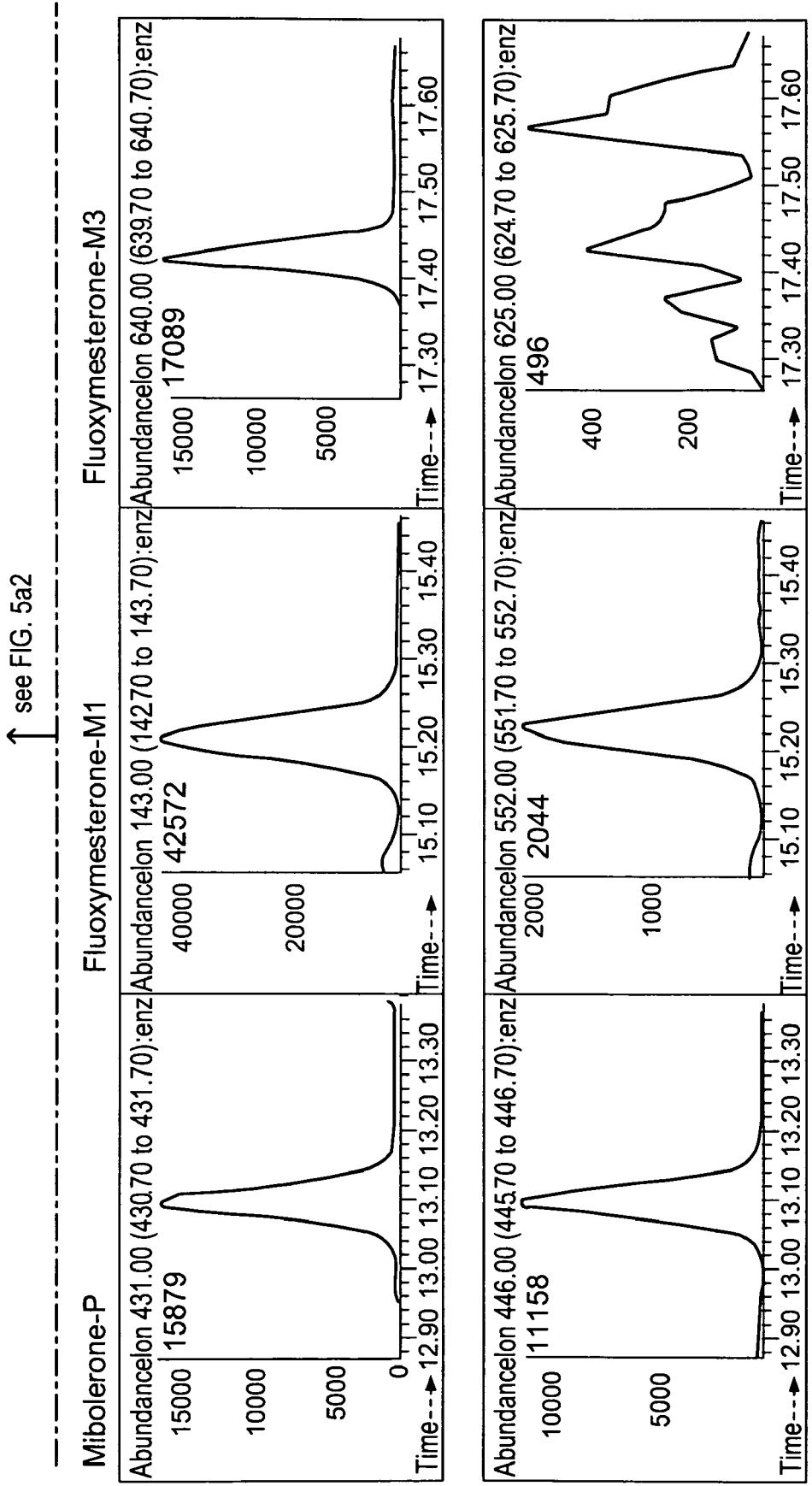
FIG. 5a3

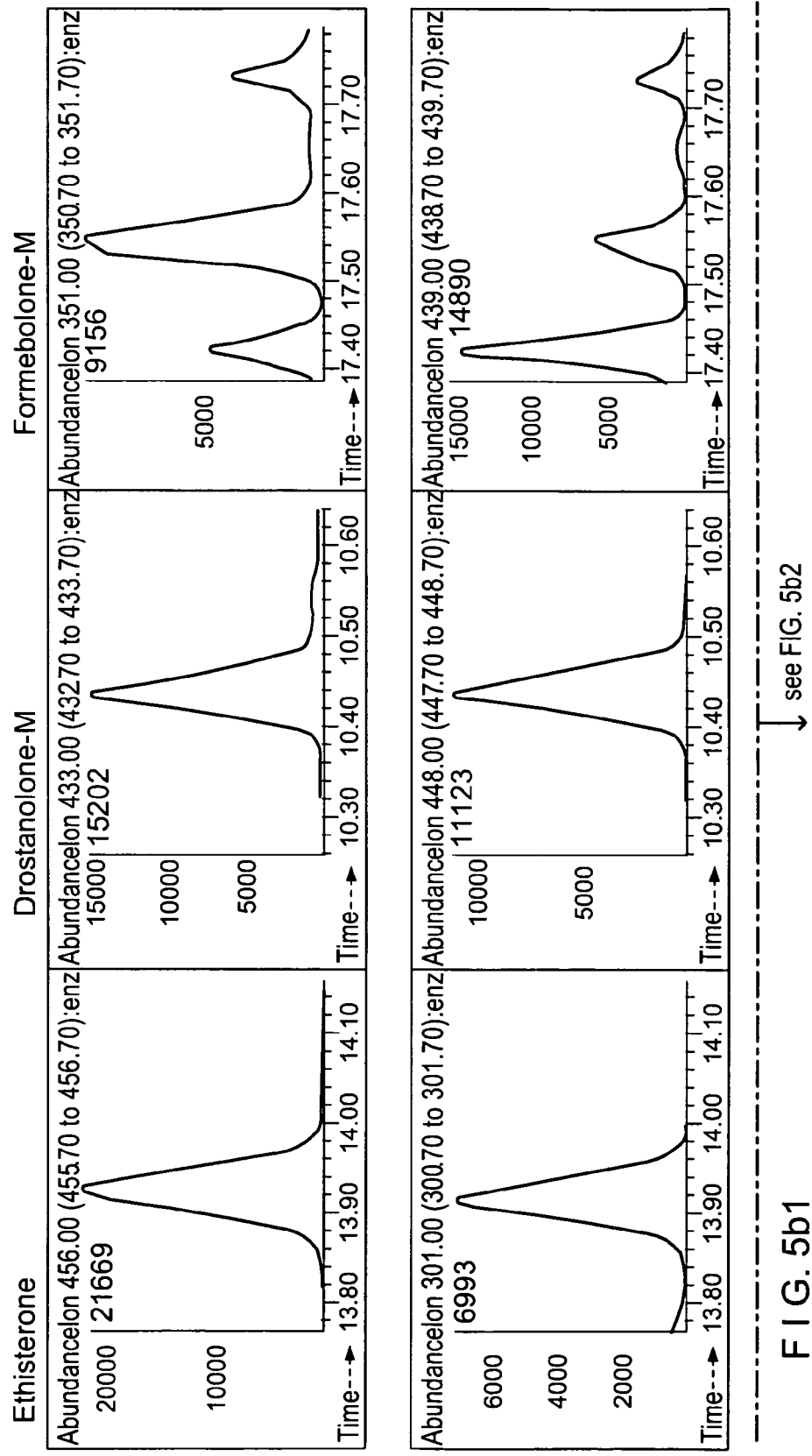
FIG. 5b1

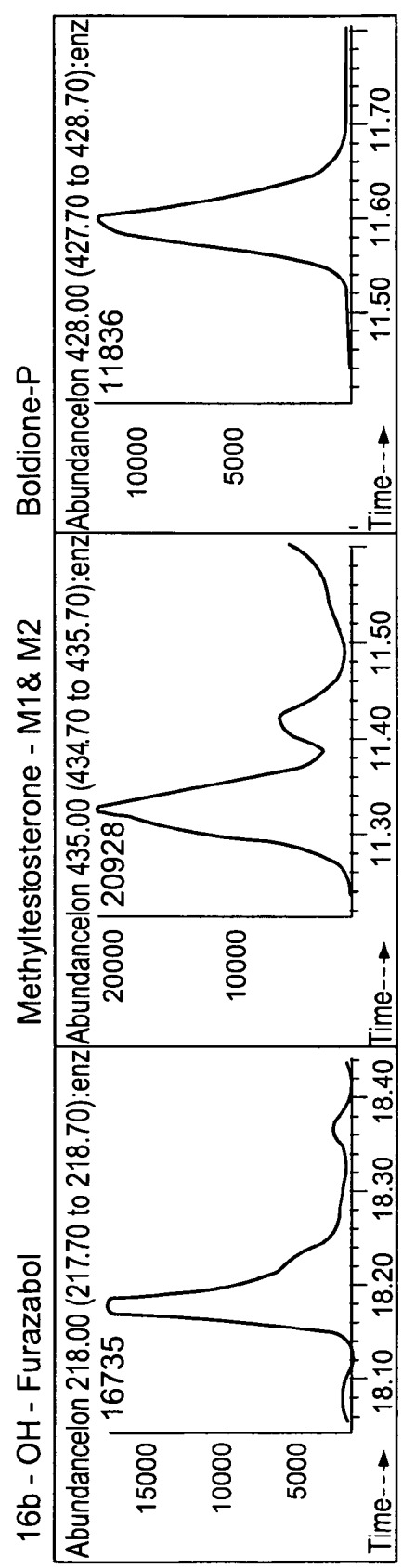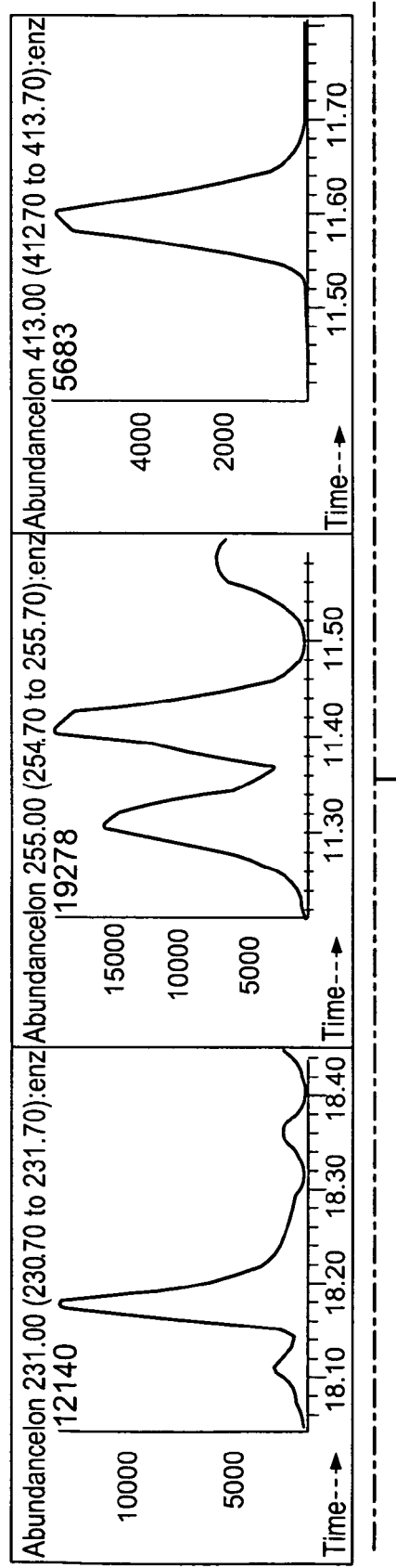
FIG. 5b2

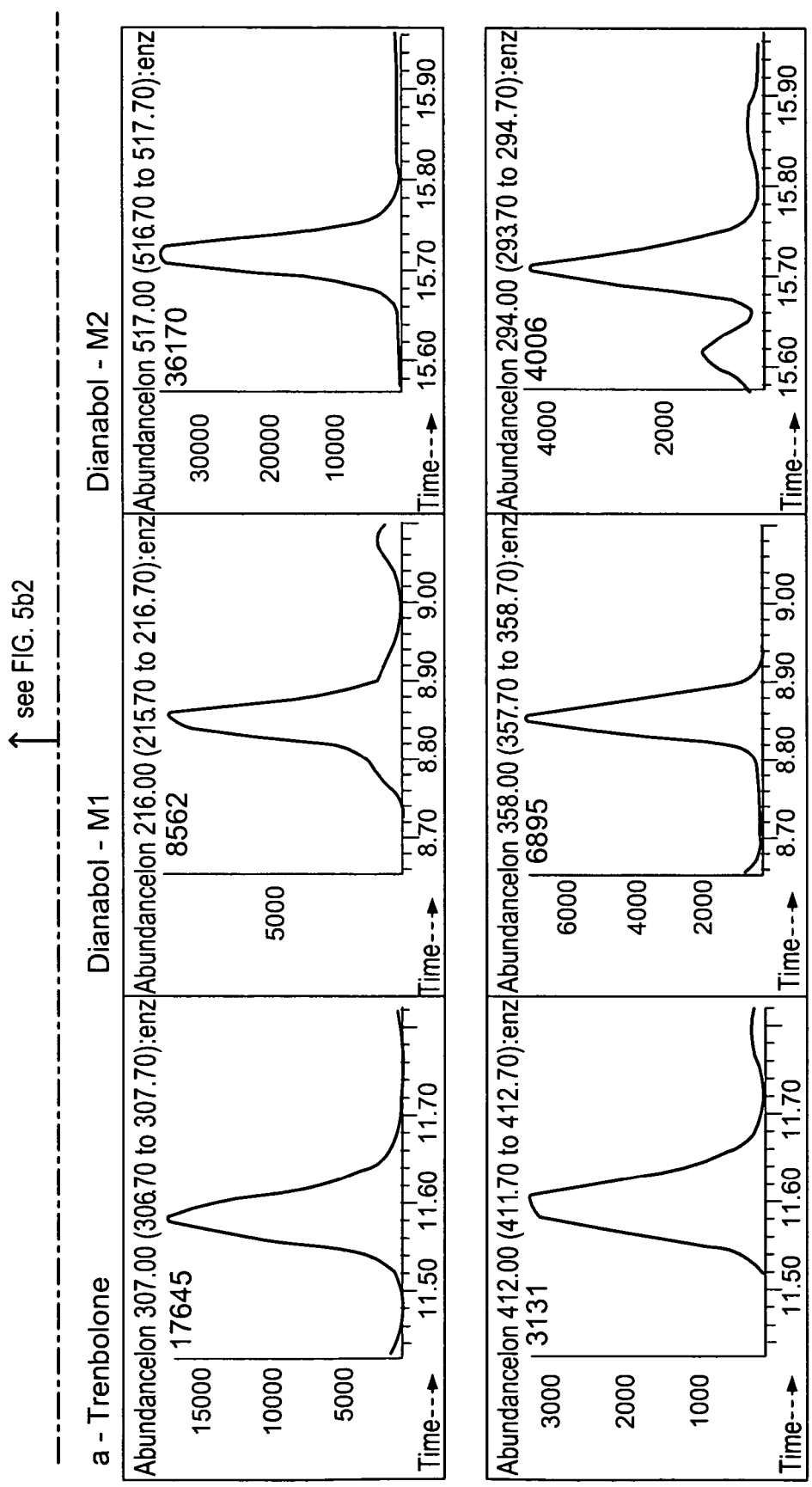
FIG. 5b3

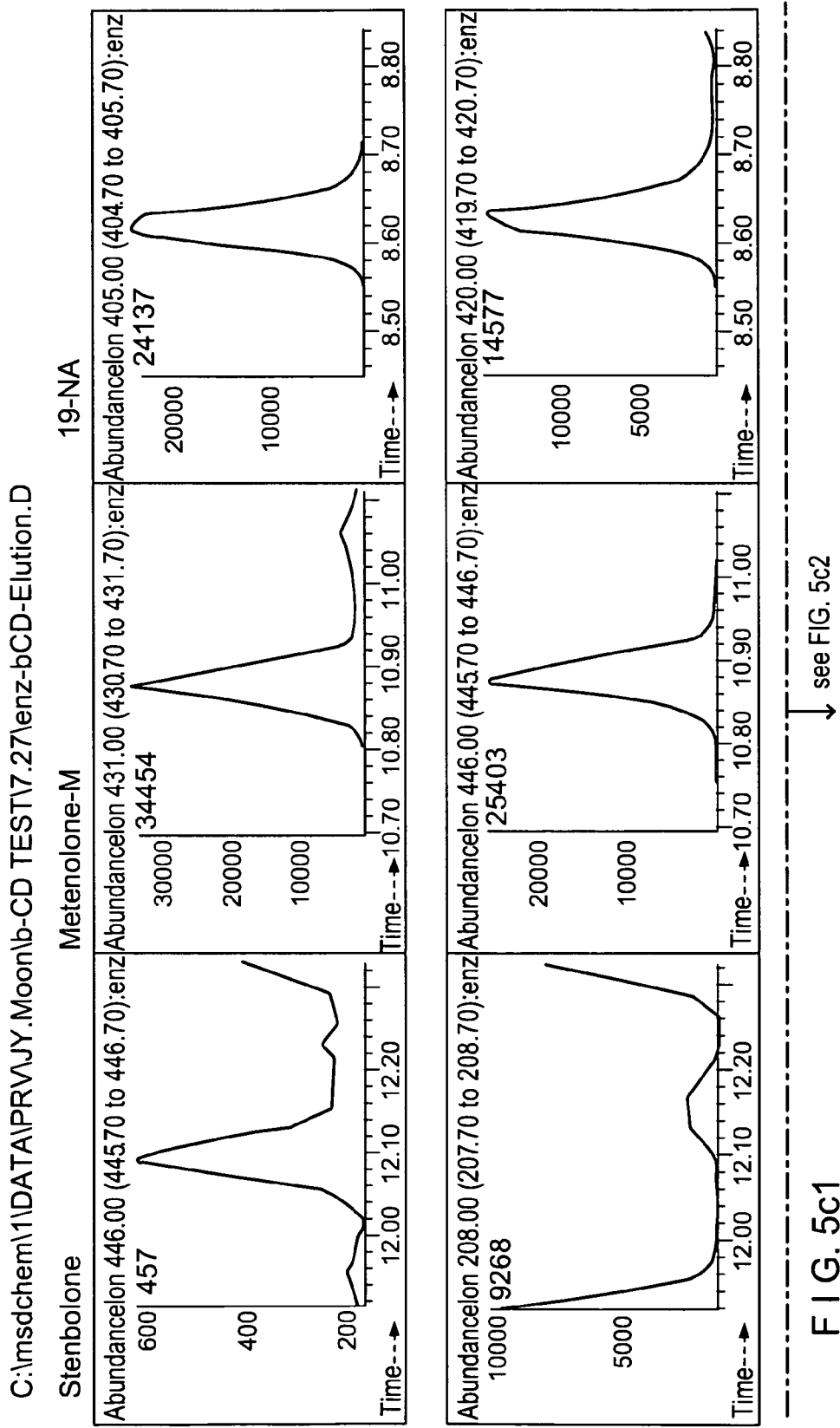
FIG. 5c1

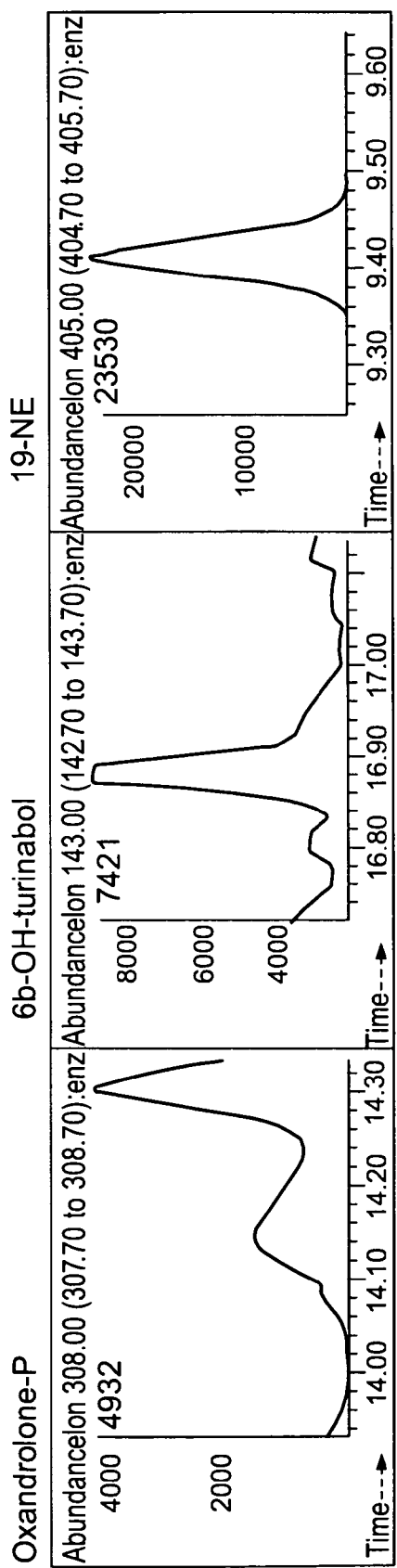
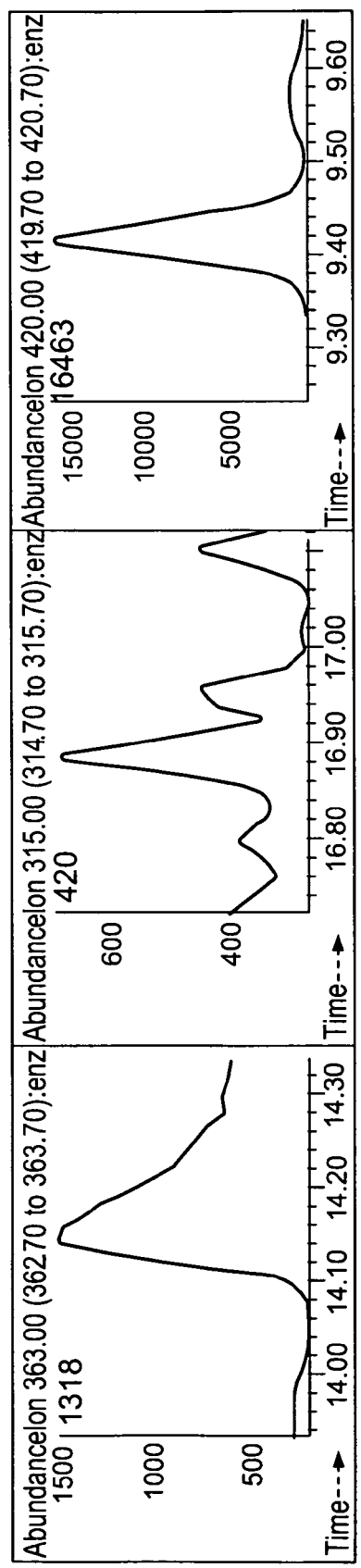
FIG. 5c2

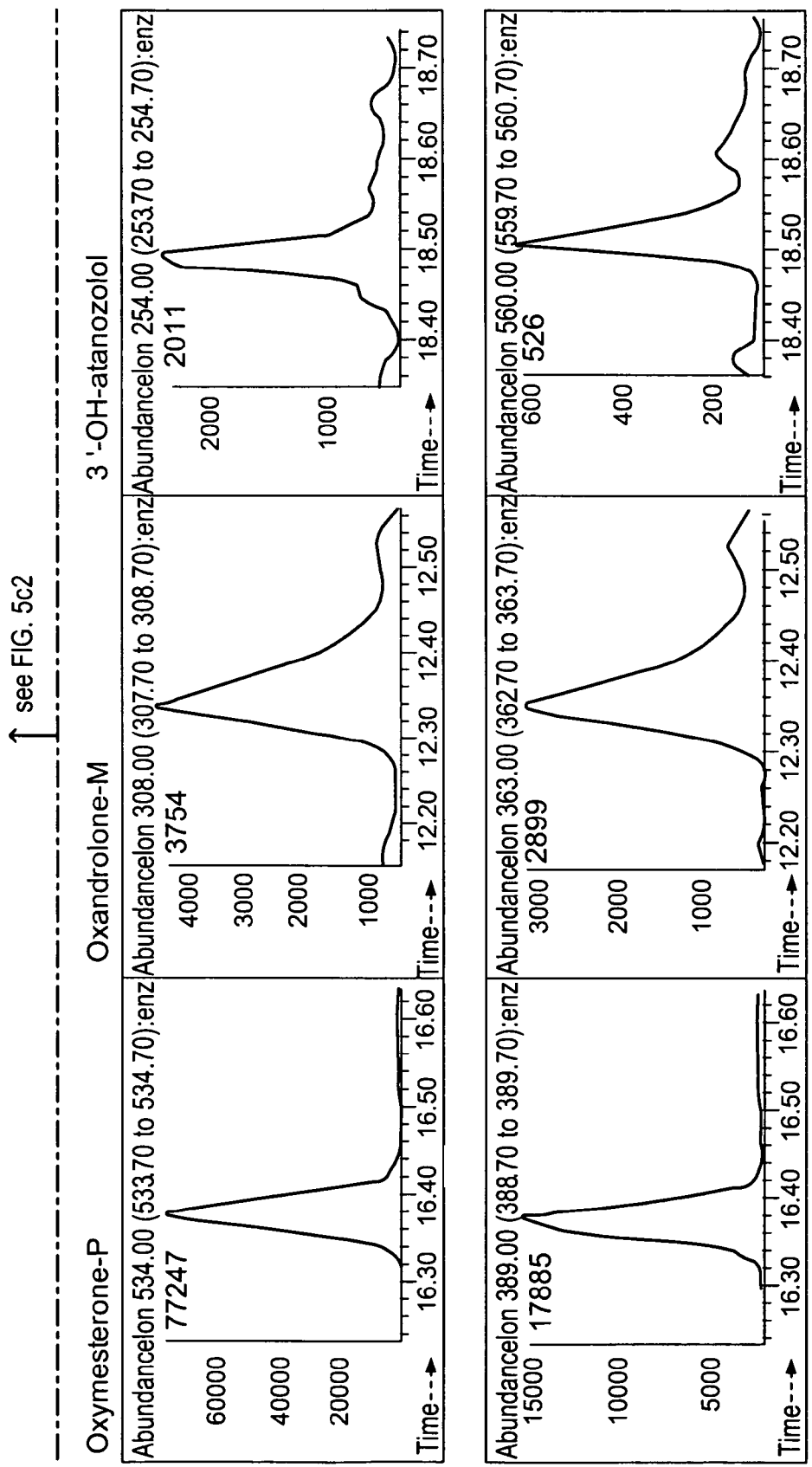
FIG. 5c3

ENTRAPPED β-CYCLODEXTRIN POLYMER AND A METHOD OF PREPARING THE SAME

CROSS-REFERENCE TO RELATED APPLICATION

This application claims priority to, and the benefit of, Korean Patent Application No. 10-2006-0119300, filed on Nov. 29, 2006, the entire disclosure of which is hereby incorporated by reference.

BACKGROUND OF THE INVENTION

1. Field of the Invention

The present invention relates to an entrapped β-cyclodextrin polymers and a method of preparing the same.

2. Description of the Related Art

In general, solid-phase extraction (SPE) via hydrophobic interactions between a packing material and an analyte has been widely used to extract steroid hormones from biological fluids such as urine and blood for clinical trials, food analyses, environmental analyses, drug tests, and doping controls for athletes (Journal of Chromatography A, 885: 3-16, 237-250, 321-341, 2000; and Rapid Communications in Mass Spectrometry, 16: 2221-2228, 2002).

In the SPE of steroid hormones using hydrophobic interactions, a modified silica such as such as C8, C18, phenyl and amino and a copolymer such as XAD (styrene-divinylbenzene copolymer) and Oasis HLB™ (divinylbenzene-N-vinylpypyrrolidone copolymer) are generally used as an adsorbent. However, the silica adsorbent has a drawback, that it is unstable at extreme pH condition during pre-treatment of the sample, becomes deactivated, and the copolymer adsorbent has a drawback that its use is limited in pre-treatment of compounds having high polarity although it is not affected by any pH conditions.

When steroid hormones extracted from biological fluids are analyzed, they are extracted by SPE in pre-treatment and separated from various interfering substances by gas or liquid chromatography combined with mass spectrometry (GC-MS or LC-MS). Reversed-phase liquid chromatography (RPLC), one of the most widely used techniques to separate steroid hormones from interfering backgrounds in the samples, also employs hydrophobic interaction (Journal of Chromatography A, 935: 141-172, 2001). Accordingly, biological substances having different chemical properties from the steroids are easily removed by SPE during the pre-treatment process. However, biological substances having similar chemical properties to the steroids are extracted with the steroids and have similar retention time during separation in RPLC.

To overcome the problems, an immuno-affinity chromatography based on biological specificity has been used (Journal of Chromatography A, 794: 37-43, 1998; Rapid Communications in Mass Spectrometry, 16: 370-374, 2002); however, it is limited because of time-consuming process to obtain antibodies of steroid hormones and the high cost of the process.

Meanwhile, β-cyclodextrin, unlike the conventional adsorbents, is capable of sequestering an organic compound having a particular structure or a steroid hormone within its inner cavity (Journal of Separation Science, 25: 789-813, 2002; Steroids, 68: 321-327, 2003).

Korean Patent Application Nos. 1997-0018599, 1997-0037127 and 1997-0037128 disclose methods of removing cholesterol, a starting substance to make steroid hormones from a liquid such as milk and cream using the property of β-cyclodextrin. However, the methods have a drawback that a small amount of β-cyclodextrin still remains even after centrifugation in the process of separating the β-cyclodextrin, to which cholesterol is adsorbed, from the liquid such as milk and cream from the liquid.

To solve the above problem, there was introduced a method to remove cholesterol having a structure similar to that of steroid hormones from milk by chemically immobilizing β-cyclodextrin onto glass beads as a SPE (Archives of Pharmaceutical Research, 27: 873-877, 2004). However, this method is not efficient because the activity of β-cyclodextrin, which is chemically immobilized onto the glass beads, is reduced due to chemical treatments and thus cholesterol cannot be removed efficiently.

In addition, there was introduced a method to increase cholesterol removal rate by forming cross-links among β-cyclodextrin molecules using epichlorohydrin as a chemical linker in an aqueous NaOH solution to increase β-cyclodextrin activity (Archives of Pharmaceutical Research, 27: 1183-1187, 2004). Various polymerized β-cyclodextrins have been prepared by applying various conditions during the cross-linking of β-cyclodextrin molecules and physical properties and activities of the β-cyclodextrin have been measured (Polymer International, 54: 744-753, 2005). However, the polymerized β-cyclodextrin prepared using the epichlorohydrin forms a gel state which becomes swollen when used in extracting steroid hormones. Thus, it gives a problem to use only a very small amount of the polymerized β-cyclodextrin in the pre-treatment relative to the amount of the sample.

SUMMARY OF THE INVENTION

As a result of intensive researches to solve the drawbacks of the conventional processes, the present inventors have found that a complex of β-cyclodextrin polymer and steroid hormones is formed in biological fluids without being swollen by adding a metal salt solution to β-cyclodextrin polymer in a gel state prepared using epichlorohydrin to entrap β-cyclodextrin polymer on the surface of the β-cyclodextrin polymer and powderizing the entrapped β-cyclodextrin polymer, and thus steroid molecules can be efficiently extracted.

The entrapped β-cyclodextrin polymers according to the present invention can be applied to prepare a packing material for solid-phase extraction. Steroid compounds can be simply separated from a complex of β-cyclodextrin by a simple method of forming the complex of β-cyclodextrin as well as steroid compounds by adding entrapped β-cyclodextrin polymers prepared according to the present invention to biological fluids containing various steroid compounds are extracted from the inclusion complex using an organic solvent.

The present invention relates to entrapped β-cyclodextrin polymers which can be used to prepare a packing material for solid-phase extraction capable of easily extracting steroid compounds.

In addition, steroid compounds can be efficiently extracted from biological samples according to the present invention. The present invention can be applied to clinical researches on various types of endocrine-dependent diseases since steroid hormones including androgen, estrogen and corticoids can be selectively extracted from biological fluids such as urine.

In addition, a sample in which steroid compounds are removed can be prepared as desired since steroid compounds can be selectively extracted according to the present invention.

In addition, the present invention can be applied to doping control of athletes since synthetic anabolic steroids can be effectively extracted.

Therefore, the present invention provides a method for preparation of entrapped β-cyclodextrin polymers easily adsorbing and desorbing steroid compounds.

According to an aspect of the present invention, there are provided entrapped β-cyclodextrin polymers, wherein metal ions are coated on the surface of the entrapped β-cyclodextrin polymers formed by the reaction of β-cyclodextrin monomers and epichlorohydrin.

According to another aspect of the present invention, there is provided a method for preparation of entrapped β-cyclodextrin polymers, the method comprising: preparing a polymer in a gel state by dissolving β-cyclodextrin in an aqueous alkali solution and adding epichlorohydrin to the solution; preparing entrapped β-cyclodextrin polymers by immersing the β-cyclodextrin polymers in a gel state in a metal salt solution followed by coating and entrapping on the surface of the β-cyclodextrin polymers; and washing, drying and pulverizing the entrapped polymer to powderize the entrapped β-cyclodextrin polymers.

According to another aspect of the present invention, there is provided a packing material for solid-phase extraction comprising the entrapped β-cyclodextrin polymers.

BRIEF DESCRIPTION OF THE DRAWINGS

The above and other features and advantages of the present invention will become more apparent by describing in detail exemplary embodiments thereof with reference to the attached drawings in which:

FIG. 1A shows a chemical structure of β-cyclodextrin and FIG. 1B schematically shows a three-dimensional structure of β-cyclodextrin;

FIG. 3A shows a scanning electron microscope (SEM) image of β-cyclodextrin, FIG. 3B shows a SEM image of entrapped β-cyclodextrin polymers prepared in Example 1, and FIG. 3C indicates a result of elemental analysis showing that Ca ions which is an entrapping agent is distributed on the surface of the β-cyclodextrin polymers;

FIGS. 4A and 4B show extracted-ion chromatograms illustrating results of chromatographic analyses of endogenous androgen and estrogen extracted from urine according to Example 2;

FIGS. 5A, 5B, 5C and 5D show extracted-ion chromatograms illustrating results of chromatographic analyses of synthetic anabolic steroid in doping control, which is extracted from urine according to Example 3.

DETAILED DESCRIPTION OF THE INVENTION

Figure 2:
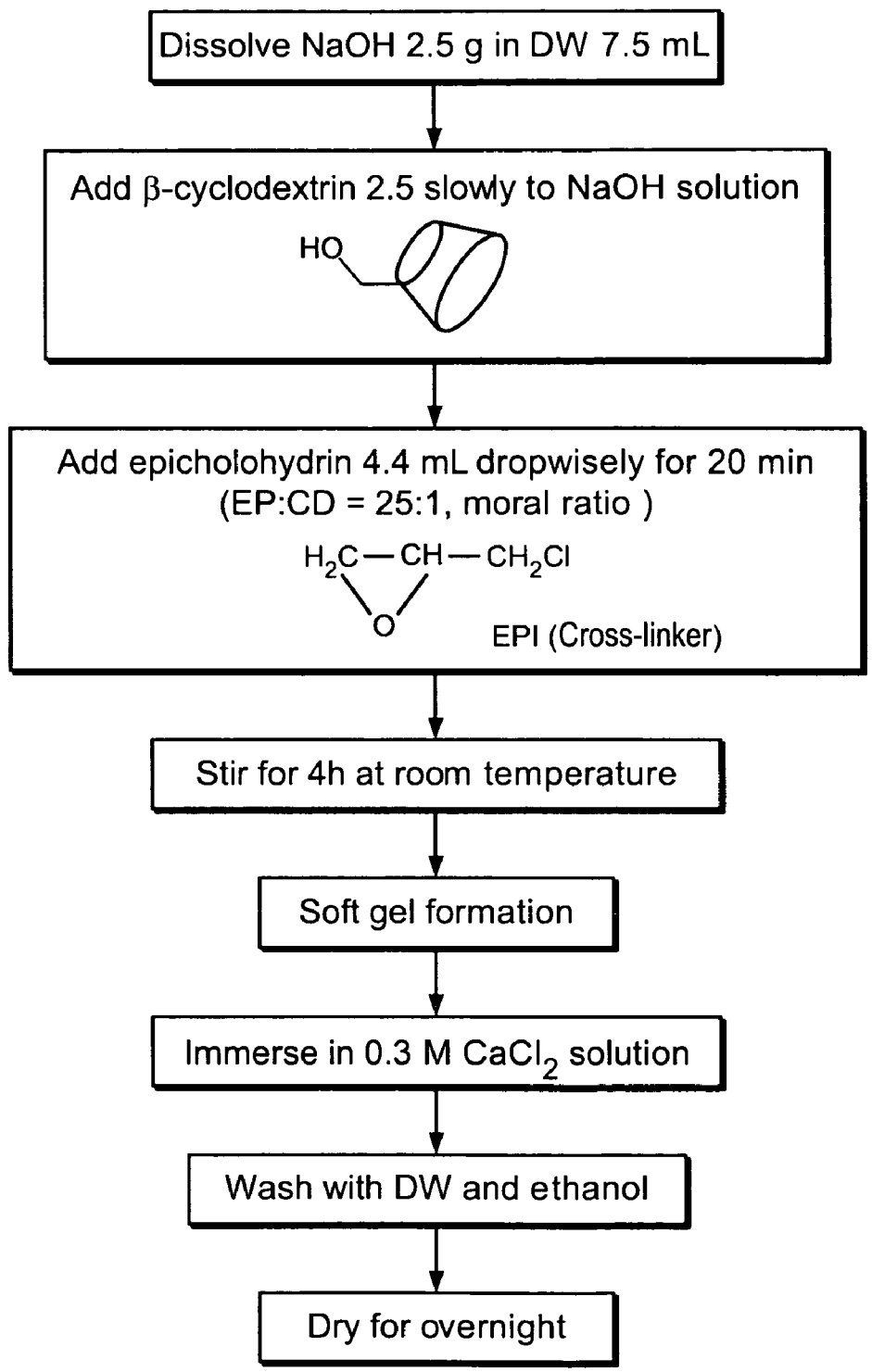
FIG. 2 shows a flow diagram for a method of preparing entrapped β-cyclodextrin polymers according to Example 1.
Figure 5D:
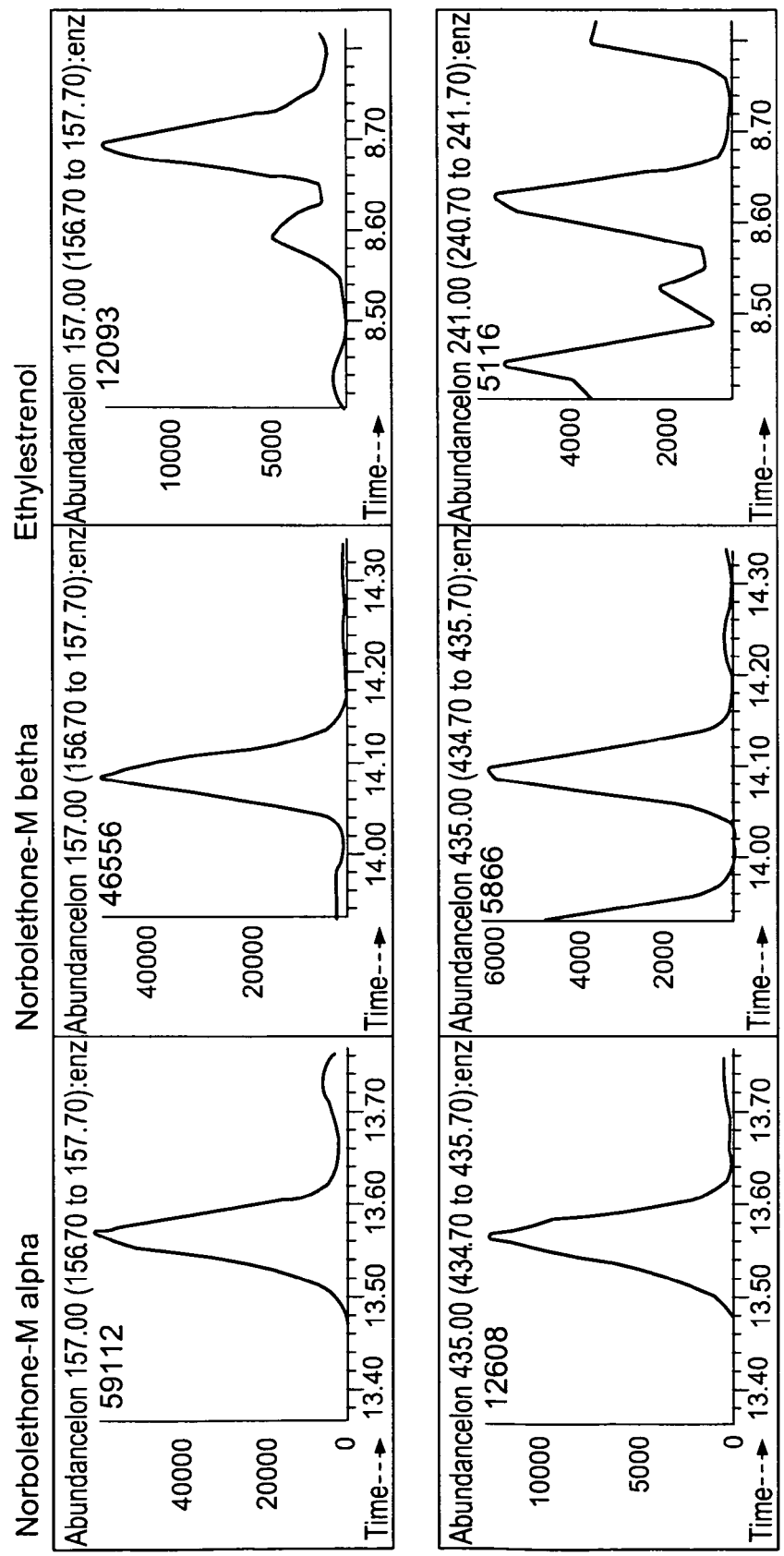

Hereinafter, the present invention will be described in detail with reference to the accompanying drawings, in which exemplary embodiments of the invention are shown.

The present invention relates to entrapped β-cyclodextrin polymers, wherein metal ions are coated on the surface of the entrapped β-cyclodextrin polymers formed by the reaction of β-cyclodextrin monomers and epichlorohydrin.

The present invention relates to a method of preparing entrapped β-cyclodextrin polymers, the method comprising:

preparing β-cyclodextrin polymers in a gel state by dissolving β-cyclodextrin in an aqueous alkali solution and adding epichlorohydrin to the solution;

preparing entrapped β-cyclodextrin polymers by immersing the β-cyclodextrin polymers in a gel state in a metal salt solution followed by coating and entrapping on the surface of the β-cyclodextrin polymers; and washing, drying and pulverizing the entrapped polymers to powderize the entrapped β-cyclodextrin polymers.

The present invention relates to a method for selective extraction of steroid compounds using entrapped β-cyclodextrin polymers. The entrapped β-cyclodextrin polymers are prepared by adding epichlorohydrin to β-cyclodextrin to prepare a polymer in a gel state, entrapping the polymer with metal ions by coating them on the surface of the polymer, and pulverizing the product.

FIGS. 1A and 1B show β-cyclodextrins used in the present invention. FIG. 1A shows a chemical structure of β-cyclodextrin and FIG. 1B schematically shows a three-dimensional structure of β-cyclodextrin. The β-cyclodextrin is α-1,4-linked cyclic oligosaccharide with seven glucose units containing hydrophilic exterior and hydrophobic interior cavity (FIG. 1A). Since a hydrophobic cavity is formed in the β-cyclodextrin and hydrophilic functional groups are exposed on the surface of the β-cyclodextrin, the β-cyclodextrin is responsible for formation of inclusion complexes with guest molecules through non-covalent interactions (FIG. B).

β-cyclodextrin becomes more widely used due to its particular structure and the property of forming an inclusion complex, but it has a problem of swelling in an aqueous solution as described above.

The present invention relates to the entrapped β-cyclodextrin polymer that is not swelled during sample preparation of urinary steroids, a method of preparing the entrapped β-cyclodextrin polymers, and various uses thereof. In the entrapped β-cyclodextrin polymers, it is formed by the reaction of β-cyclodextrin monomers and epichlorohydrin followed by entrapment of metal ions.

A method of preparing entrapped β-cyclodextrin polymers according to the present invention includes: preparing a polymer in a gel state by dissolving β-cyclodextrin in an aqueous alkali solution and adding epichlorohydrin to the solution; entrapping the polymer by immersing the polymer in a metal solution; and washing, drying and pulverizing the entrapped polymer to prepare products.

First, cross-links are formed among β-cyclodextrin monomers using epichlorohydrin in order to bind the β-cyclodextrin monomers. Herein, the β-cyclodextrin monomers are dissolved in an aqueous alkali solution to be used.

The alkali aqueous solution may be prepared using an alkali metal hydroxide, such as NaOH and KOH. If they have the same concentration, it is preferred to us NaOH solution because it has higher reactivity than KOH solution. Then, metal ions are introduced into the process of curing the polymerized β-cyclodextrin in the gel state in which cross-links are formed. The metal ions may be Ca or Na and a salt form of the metal is introduced into the process. The metal salt may be selected from the group consisting of $CaCl_2$, NaCl, $Ca(NO_3)_2$ and $CaSO_4$, and $CaCl_2$ is used to achieve the fast immersion of polymer if the metal salts have the same concentration.

The concentration of the metal salt solution may be in the range of 0.05 to 1.0 M, preferably 0.2 to 0.3 M. When the concentration is within the range above, the metal ions can be efficiently interposed between the cross-linked β-cyclodextrin layers.

Metal ions can be interposed between the cross-linked β-cyclodextrin layers using the halogenated metal salts. FIGS. 3B and 3C show the Ca ions interposed between the layers. When the metal ions are interposed between the layers, the swelling does not occur any more and the selective binding of β-cyclodextrin to steroid compounds can be enhanced.

The entrapped β-cyclodextrin polymers sufficiently washed with ethanol and water, dried at a temperature in the range of 50 to 70° C., and pulverized using a variety of methods to prepare the products. Here, the entrapped β-cyclodextrin polymers have a diameter in the range of 100 to 500 μm, preferably about 200 μm.

Thus prepared products of the present invention easily form a β-cyclodextrin-steroid compound complex since they can be selectively bound to a compound having a steroid structure. In addition, inclusive steroids are easily isolated with an organic solvent and evaporating the organic solvent.

Since the entrapped β-cyclodextrin polymers can extract and isolate various compounds having the steroid structure from biological fluids, it can be used to a variety of fields in which the steroid compound needs to be selectively isolated or removed.

For example, the entrapped β-cyclodextrin polymers of the present invention can be used as a packing material of a cartridge for solid-phase extraction (SPE). Here, the particle size of the powders is required to be uniform in order to maximize extraction efficiency.

A method for preparing entrapped β-cyclodextrin polymers according to an embodiment of the present invention is schematically shown in FIG. 2.

Meanwhile, a method for extraction of steroid compounds using the products according to the present invention will be described.

First, a liquid sample containing steroid compounds is diluted using a phosphate buffer solution and an enzyme is added to hydrolyze. The sample may be a liquid containing steroid compounds, for example, urine, blood, a tissue extract and a cell culture medium, which can be diluted using water or a phosphate buffer solution to prepare a solution in a state similar to urine (Rapid Communications in Mass Spectrometry, 16: 2221-2228, 2002), and extracted in the same manner used in urine.

Here, the amount of entrapped β-cyclodextrin polymers may be in the range of 0.2 to 0.5 g per 1 mL of the urine sample. The enzyme may be β-glucuronidase or a mixture of β-glucuronidase and arylsulfatase, and the amount may be in the range of 80 to 140 unit/mL.

The entrapped β-cyclodextrin polymers are added to the sample, and the mixture is stirred and centrifuged at 1,500 rpm or higher.

The entrapped β-cyclodextrin polymers are isolated by filtration, and a phosphate buffer solution and at least one polar organic solvent selected from the group consisting of tetrahydrofuran (THF), ethyl acetate and ether or a mixture are added. The pH of the mixture is adjusted to 9.0 to 10.0 using 5% $K_2CO_3$ aqueous solution. The adjusted pH range should be in optimum state in order to extract steroid hormones from the sample upon considering pKa values of an analyte. When the pH is not within the range above, extraction efficiency is considerably decreased.

The steroid compound is then extracted by shaking the mixture. Here, the organic solvent may be at least one selected from the group consisting of ethyl acetate, n-hexane and ether or a mixture thereof. The amount of the organic solvent is minimized to the extent to separate compounds dissolved in the polar organic solvent such as THF from the aqueous solution.

According to the method of extracting steroid compounds of the present invention, various compounds having a steroid structure can be easily extracted, and more particularly, cholesterol, steroid hormones including an endogenous androgen and estrogen, synthetic anabolic steroids taken by athletes for the purpose of strengthening muscles, corticoids, and the like can be selectively extracted.

The endogenous androgen may be dihydrotestosterone (DHT), dehydroepiandrosterone (DHEA), testosterone, 5α-androstane-3α, 17β-diol, androstenedione, epitestosterone, 5α-androstane-3β, 17β-diol, androstenediol, androsterone, etiocholanolone, 11-keto-androsterone (11-keto-A), 11-keto-etiocholanolone (11-keto-E), 11-hydroxy-androsterone (11-OH-A), 11-hydroxy-etiocholanolone (11-OH-E) or 5α-androstanedione, but is not limited thereto.

In addition, the estrogen may be estrone, 17β-estradiol, estriol, 2-hydroxy-estrone (2-OH-E1), 2-hydroxy-estradiol (2-OH-E2), 17-epiestriol, 4-hydroxy-estrone (4-OH-E1), 4-hydroxy-estradiol (4-OH-E2), 2-methoxy-estrone (2-MeO-E1), 2-methoxy-estradiol (2-MeO-E2) or 16α-hydroxy-estrone (16α-OH-E1), but is not limited thereto.

The synthetic anabolic steroids may be calusterone, bolasterone, boldenone, clostebol, mibolerone, fluoxymesterone, ethisterone, drostanolone, formebolone, 16β-hydroxy-furazabol, methyltestosterone, boldione, α-trenbolone, dianabol, stenbolone, metenolone, 19-norandrosterone (19-NA), 19-noretiocholanolone (19-NE), oxandrolone, 6β-hydroxy-furinabol, oxymesterone, 3'-hydroxy-stanozolol, norbolethone, ethylestrenol, gestrinone, tetrahydrogestrinone, or metabolites thereof, but is not limited thereto.

In addition, corticoids included in a small amount in urine can also be simultaneously extracted from urine. The corticoids may be triamcinolone, prednisolone, prednisone, fluochlorocortisone, 6α-methylprednisolone, betamethasone, dexamethasone, flumethasone, beclomethasone, triamcinolone acetonide, desonide, flunisolide, flurandrenolide, fluocinolone acetonide, desoximethasone, budesonide, flucinonide, amcinonide, cortisol, or cortisone, but is not limited thereto.

According to the present invention, steroid compounds can be simply separated from an inclusion complex of β-cyclodextrin with steroid compounds using a simple method of forming the complex of β-cyclodextrin and steroid compounds by adding entrapped β-cyclodextrin polymers prepared according to the present invention to the biological samples containing various steroid compounds and extracting the steroid compounds from the complex using an organic solvent.

In addition, the present invention can be efficiently applied to clinical research on various endocrine-dependent diseases since steroid hormones including androgen, estrogen, corticoids, or the like can be selectively extracted from biological fluids such as urine. A sample in which the steroid compound is removed can also be prepared.

In addition, doping control of athletes can be efficiently performed according to the present invention since synthetic anabolic steroids can be efficiently extracted.

In addition, the entrapped β-cyclodextrin polymers used to extract the steroid compounds can be recovered and reused after being washed with an organic solvent.

The present invention will now be described in more detail with reference to the following examples. The following examples are for illustrative purposes only and are not intended to limit the scope of the invention.

Example 1

Method of Preparing Entrapped β-cyclodextrin Polymers 2.5 g of β-cyclodextrin was dissolved in a NaOH solution (2.5 g/7.5 mL), and 4.4 mL of epichlorohydrin was gradually added to the solution for 20 minutes. The mixture was stirred at room temperature for 4 hours. The resultant polymer in a gel state was immersed in a 0.3 M $CaCl_2$ solution to be cured. Then, the cured polymer was sufficiently washed with water and ethanol, dried at 70° C., and pulverized using a pulverizer to prepare entrapped β-cyclodextrin polymers having an average particle diameter of 200 μm (FIG. 2).

Experimental Example 1

Identification of Polymerized β-cyclodextrin

Structures of β-cyclodextrin and entrapped β-cyclodextrin polymers prepared according to Example 1 were identified by 3000× magnification at 15 kV using a scanning electron microscope (SEM), and the results are shown in FIGS. 3A and 3B.

While the non-polymerized β-cyclodextrin particles were uniformly distributed as shown in FIG. 3A, the entrapped β-cyclodextrin polymers prepared according to Example 1 were cross-linked to each other as shown in FIG. 3B. In addition, as shown in FIG. 3C, Ca ion particles derived from $CaCl_2$ were distributed on the surface of β-cyclodextrin polymers.

Example 2

Method of Extracting Steroid Compounds Using Entrapped β-cyclodextrin Polymers 2 mL of urine was mixed with 1 mL of 0.2 M phosphate buffer solution (pH 7.2), and 50 μL of β-glucuronidase was added thereto to hydrolyze the urine. 0.5 g of the entrapped β-cyclodextrin polymers prepared in Example 1 was added thereto, and the mixture was stirred for 10 minutes. Then, the mixture was centrifuged at 3000 rpm for 8 minutes to isolate entrapped β-cyclodextrin polymers.

1 mL of a phosphate buffer solution and 3 mL of tetrahydrofuran (THF) was added to isolated polymers, and the mixture was stirred for 10 minutes. 0.7 mL of 0.5% $K_2CO_3$ solution was added thereto to adjust the pH of the solution to 9.6, and 2 mL of a mixed solution of ethyl acetate and n-hexane (2:3, v/v) was added to the mixture to extract androgen and estrogen contained in the powders.

The extracted androgen and estrogen were reacted with 50 μL of a derivative reagent (MSTFA/$NH_4$I/DTE, 1000:4:5, v/w/w) at 60° C. for 20 minutes, and analyzed by a selected-ion monitoring (SIM) mode using GC-MS under conditions described below.

Instrument(s): Agilent 6890 GC and Agilent 5973N Mass Selective Detector
Column: Ultra-2 fused-silica capillary column
  (Agilent Technologies; length 25 m, inner diameter: 0.2 mm, thickness: 0.33 μm)
Injector Temperature: 280° C.
Carrier Gas: Helium (0.8 mL/min)
Injection amount: 2 μL
Injection Mode: 10:1 split mode
Oven Temperature: The temperature of the oven was increased from 200° C. to 260° C. at a rate of 2° C. per minute, maintained for 5 minutes, and increased to 280° C. at a rate of 4° C. per minute. Then, the temperature was increased to 310° C. at a rate of 15° C. per minute, and maintained for 3 minutes.
Temperatures of Source and Analyzer: 230° C. and 300° C.
Ionization: Electron impact ionization (EI)
Ionization Energy: 70 eV
Characteristic Ions for Analysis: m/z 434, 432, 436, 430, 421, 419, 520, 522, 458, 414, 416, 504, 502, 487, 444, 446

Qualitative chemical analyses of the compounds were performed based on a single characteristic ion with retention time in the column. 4 to 11 ions from each of 6 groups were simultaneously analyzed. The results are shown in FIGS. 4A and 4B.

That is, cholesterol and 15 endogenous androgens, such as dihydrotestosterone (DHT), dehydroepiandrosterone (DHEA), testosterone, 5α-androstane-3α, 17β-diol, androstenedione, epitestosterone, 5α-androstane-3α,17β-diol, androstenediol, androsterone, etiocholanolone, 11-keto-androsterone (11-keto-A), 11-keto-etiocholanolone (11-keto-E), 11-hydroxy-androsterone (11-OH-A), 11-hydroxy-etiocholanolone (11-OH-E), and 5α-androstanedione; and 11 estrogens, such as estrone, 17β-estradiol, estriol, 2-hydroxy-estrone (2-OH-E1), 2-hydroxy-estradiol (2-OH-E2), 17-epi-estriol, 4-hydroxy-estrone (4-OH-E1), 4-hydroxy-estradiol (4-OH-E2), 2-methoxy-estrone (2-MeO-E1), 2-methoxy-estradiol (2-MeO-E2), and 16α-hydroxy-estrone (16α-OH-E1), were selectively extracted from the urine sample. As a result, recovery rates of 15 androgens and 11 estrogens were in the range of 92 to 126%.

The recovery rates (same as recovery rates measured in Examples 3 to 4) were calculated by comparing the results of analyses and concentrations of the same steroid hormones before and after extraction.

It was confirmed that the method of extracting steroid compounds using entrapped β-cyclodextrin polymers has excellent efficiency as compared to those of conventional methods disclosed in Journal of Chromatography A, 885: 3-16, 237-250, 321-341, 2000; and Rapid Communications in Mass Spectrometry, 16: 2221-2228, 2002.

In addition, extraction rate of the cholesterol was 96%. In particular, although various technologies of removing cholesterol from samples have been reported (Archives of Pharmaceutical Research, 27: 873-877, 2004; and Archives of Pharmaceutical Research, 27: 1183-1187, 2004), the method of extracting cholesterol using entrapped β-cyclodextrin polymers prepared according to the present invention is known most effective in removing cholesterol from biological samples with a cholesterol removal rate of up to 98%.

Example 3

Method of Extracting Synthetic Anabolic Steroids Using Entrapped β-cyclodextrin Polymers 2 mL of urine was mixed with 1 mL of 0.2 M phosphate buffer solution (pH 7.2), and 50 μL of β-glucuronidase was added thereto to hydrolyze the urine. 0.5 g of entrapped β-cyclodextrin polymers was added thereto, and the mixture was stirred for 10 minutes. Then, the mixture was centrifuged at 3000 rpm for 8 minutes to isolate polymers. 1 mL of a phosphate buffer solution and 3 mL of THF were added to the separated powders, and the mixture was stirred for 10 minutes. Then, 0.7 mL of 0.5% $K_2CO_3$ solution was added thereto to adjust the pH of the solution to 9.6, and 2 mL of diethyl-ether was added to the mixture to extract synthetic anabolic steroids contained in the powders. The extracted synthetic anabolic steroids were reacted with 50 μL of a polymerization reagent (MSTFA/NH$_4$I/DTE, 1000:4:5, v/w/w) at 60° C. for 20 minutes, and analyzed using GC-SIM/MS under conditions described below.

Instrument(s): Agilent 6890 GC and Agilent 5975 Mass Selective Detector

Column: Ultra-1 fused-silica capillary column
(Agilent Technologies; length 17 m, inner diameter 0.2 mm, thickness 0.11 μm)

Injector Temperature: 280° C.

Carrier Gas: Helium (0.6 mL/min)

Injection Amount: 2 μL

Injection Mode: 10:1 split mode

Oven Temperature: The temperature of the oven was increased from 180° C. to 260° C. at a rate of 4° C. per minute, increased to 320° C. at a rate of 15° C. per minute, and maintained for 3.67 minutes.

Temperatures of Source and Analyzer: 230° C. and 300° C.

Ionization: Electron impact ionization (EI)

Ionization Energy: 70 eV

Characteristic Ions for Analysis: Two characteristic ions for a compound which is capable of representing their chemical structures were selected, and 11 groups were analyzed under conditions described below. 1 (14), 2 (21), 3 (21), 4 (20), 5 (20), 6 (25), 7 (21), 8 (30), 9 (27), 10 (23), 11 (25)

Qualitative chemical analyses of the compounds were performed based on two characteristic ions with retention time in the column. The results are shown in FIGS. 5A, 5B, 5C and 5D.

That is, 30 synthetic anabolic steroids such as calusterone, bolasterone, boldenone, clostebol, mibolerone, fluoxymesterone, ethisterone, drostanolone, formebolone, 16β-hydroxy-furazabol, methyltestosterone, boldione, α-trenbolone, dianabol, stenbolone, metenolone, 19-norandrosterone (19-NA), 19-noretiocholanolone (19-NE), oxandrolone, 6β-hydroxy-furinabol, oxymesterone, 3'-hydroxy-stanozolol, norbolethone, ethylestrenol, or metabolites thereof were selectively extracted from the urine sample for doping tests of athletes. As a result, extraction rates of the synthetic anabolic steroids were in the range of 84 to 131%.

The extraction rates of the synthetic anabolic steroids included in urine which was obtained in Example 3 had constant values compared to extraction rates obtained according to conventional SPE in which the extraction rates vary according to polarity of compounds Particularly, extraction rates of steroid hormones having high polarity such as metabolites of fluoxymesterone and oxandrolone were about 40% in SPE using hydrophobic interaction, while extraction rates thereof were in the range of 91 to 105% according to Example 3. Thus, it was confirmed a high yield could be obtained not by polarity of compounds but structural properties of compounds.

Example 4

Method of Extracting Synthetic Anabolic Steroids and Corticoids Using Entrapped β-cyclodextrin Polymers 2 mL of urine was mixed with 1 mL of 0.2 M phosphate buffer solution (pH 7.2), and 50 μL of β-glucuronidase was added thereto to hydrolyze the urine. 0.5 g of entrapped β-cyclodextrin polymers was added thereto, and the mixture was stirred for 10 minutes. Then, the mixture was centrifuged at 3000 rpm for 8 minutes to isolate the polymers.

1 mL of a phosphate buffer solution and 3 mL of THF were added to the separated entrapped β-cyclodextrin polymers, and the mixture was stirred for 10 minutes. Then, 0.7 mL of 0.5% K$_2$CO$_3$ solution was added thereto to adjust the pH of the solution to 9.6, and 2 mL of diethylether was added to the mixture to extract corticoids contained in the entrapped β-cyclodextrin polymers. The extracted corticoids were dissolved in 100 μL of 50% acetonitrile solution prepared by 0.1% of acetic acid, and analyzed using LC-tandem mass spectrometry (LC-MS/MS) under conditions described below.

Instrument(s): Surveyor HPLC & TSQ Quantum Discovery MAX

Column: Hypersil Gold
(ThermoFinnigan; length 50 mm, inner diameter: 2.1 mm, particle size: 1.9 μm)

Mobile Phase: A (0.1% acetic acid in 5% acetonitrile)
B (0.06% acetic acid in 95% acetonitrile)

Injection Amount: 5 μL

Ionization: electrospray ionization (ESI) in the positive mode

Analysis Mode: Single Reaction Monitoring (SRM), 0.02 sec/scan

Spray Voltage: 4500 V

Peak Width: Q1 (0.5) & Q3 (0.7)

Velocity of Mobile Phase: 0.3 mL/min

Figure 6A:
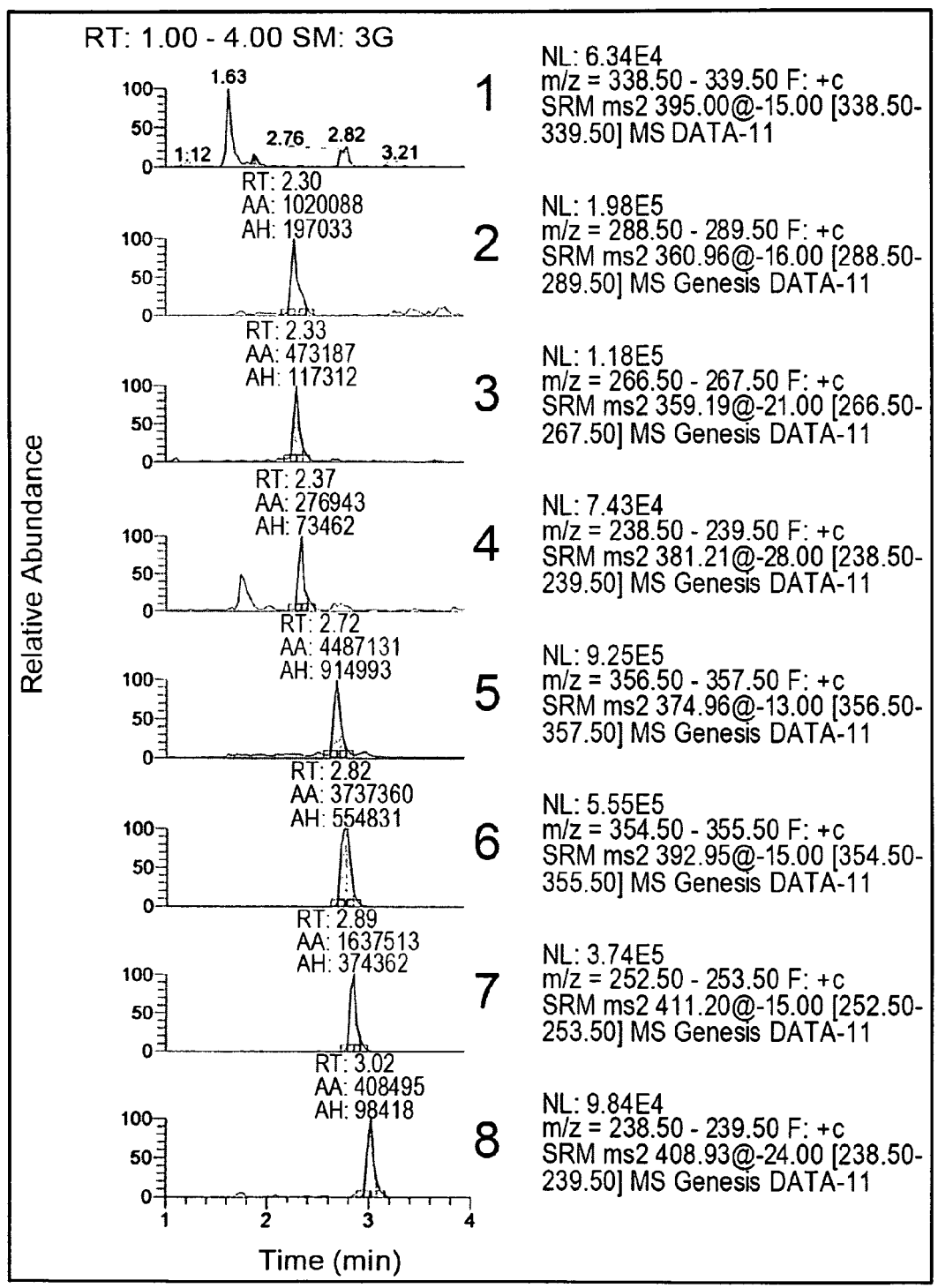
FIG. 6 shows chromatograms illustrating results of chromatographic analyses of urinary corticoids according to Example 4.
Figure 6B:
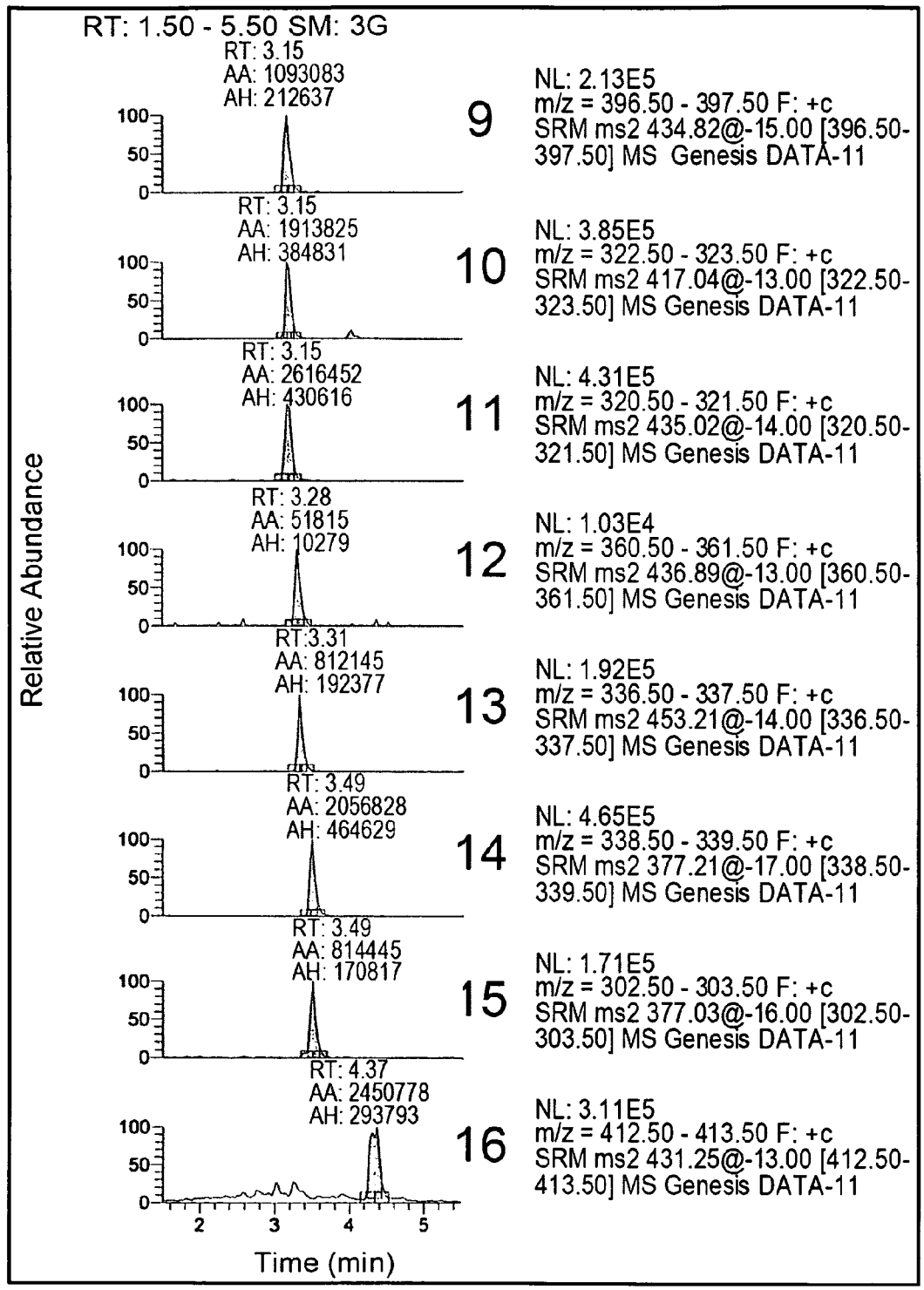
Figure 6C:
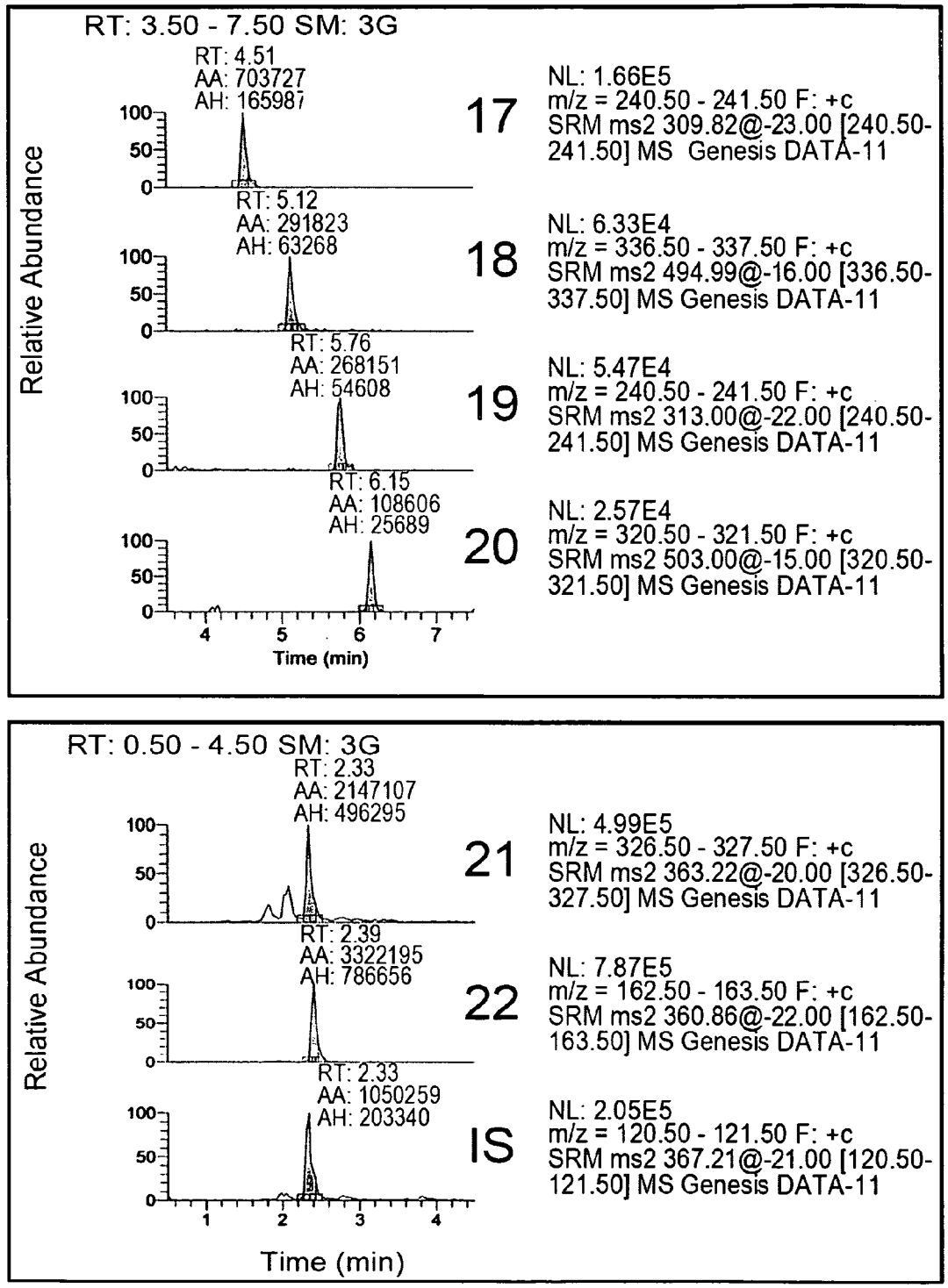

Mobile Phase Change: Mobile phase was changed from initial state of 90% (A) to 10% (A) for 2 minutes, maintained for 1 minute, and returned to the initial state of 90% (A) for 5 minutes. The analysis results of two synthetic anabolic steroids (17: gestrinone and 20: tetrahydrogestrinone) and 21 corticoids included in the urine sample were shown in FIG. 6.

That is, extraction rates of two synthetic anabolic steroids (17: gestrinone and 20: tetrahydrogestrinone) and 21 corticoids (1: triamcinolone, 2: prednisolone, 3: prednisone, 4: fluochlorocortisone, 5: 6α-methyl-prednisolone, 7: betamethasone & dexamethasone, 8: flumethasone, 9: beclomethasone, 10: triamcinolone acetonide, 11: desonide, 12: flunisolide, 13: flurandrenolide, 14: fluocinolone acetonide, 15: desoximethasone, 16: budesonide, 18: flucinonide, 19: amcinonide, 21: cortisol, 22: cortisone, 12: internal standard, and d$_4$-cortisol) included in the urine sample were in the range of 72 to 119%. It was confirmed that the results were complimentary when compared to a conventional liquid-liquid extraction (Rapid Communications in Mass Spectrometry, 17: 2107-2114, 2003).

Example 5

Packing Material for Solid-Phase Extraction Using Cured Polymerized β-cyclodextrin Powders Solid-phase extraction was performed using the cured polymerized β-cyclodextrin powders having an average diameter of 200 μm prepared in Example 1 as a packing material. As a result, swelling did not occur.

Comparative Example

Packing Material for Solid-Phase Extraction Using Entrapped β-cyclodextrin Polymers Solid-phase extraction was performed using entrapped β-cyclodextrin polymers with an average diameter of 200 μm which was not entrapped with metal ions as a packing material. As a result, swelling occurred.

As describe above, according to the present invention, various types of steroid compounds can be selectively separated from the samples for clinical trials, food analyses, environmental analyses, drug tests, and doping control of athletes by a simple process.

In addition, entrapped β-cyclodextrin polymers prepared according to the present invention can be used as a packing material for solid-phase extraction. When steroid compounds are extracted, steroid compounds can be simply extracted by adding an organic solvent to a complex of β-cyclodextrin and steroid compounds without using an additional device, which is distinct from conventional solid-phase extraction.

In addition, the entrapped β-cyclodextrin polymers have high economical values since the powders can be washed with an organic solvent and reused.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of preparing entrapped β-cyclodextrin polymers, the method comprising:
    preparing β-cyclodextrin polymers in a gel state by dissolving β-cyclodextrin in an aqueous alkali solution and adding epichlorohydrin to the solution;
    preparing entrapped β-cyclodextrin polymers by immersing the β-cyclodextrin polymers in a gel state in a metal salt solution followed by entrapping on the surface of the β-cyclodextrin polymers; and
    washing, drying and pulverizing the entrapped polymers to powderize the entrapped β-cyclodextrin polymers
    wherein the metal salt is selected from the group consisting of $CaCl_2$, $NaCl$, $Ca(NO_3)_2$ and $CaSO_4$.

2. The method of claim 1, wherein the alkali aqueous solution is prepared using an alkali metal hydroxide.

3. The method of claim 2, wherein the alkali metal hydroxide is NaOH or KOH.

4. The method of claim 1, wherein the concentration of the metal salt solution is in the range of 0.2 to 0.3 M.

* * * * *